(12) United States Patent
Gaik-Lim Khoo et al.

(10) Patent No.: US 7,700,582 B2
(45) Date of Patent: *Apr. 20, 2010

(54) PHARMACEUTICAL FORMULATION

(75) Inventors: Cynthia Gaik-Lim Khoo, Höllviken (SE); Helena Gustafsson, Göteborg (SE)

(73) Assignee: AstraZeneca AB, Sodertalje (SE)

( * ) Notice: Subject to any disclaimer, the term of this patent is extended or adjusted under 35 U.S.C. 154(b) by 1290 days.

This patent is subject to a terminal disclaimer.

(21) Appl. No.: 10/481,232

(22) PCT Filed: Jun. 19, 2002

(86) PCT No.: PCT/SE02/01217

§ 371 (c)(1),
(2), (4) Date: Jul. 23, 2004

(87) PCT Pub. No.: WO03/000293

PCT Pub. Date: Jan. 3, 2003

(65) Prior Publication Data

US 2004/0242536 A1    Dec. 2, 2004

(30) Foreign Application Priority Data

Jun. 21, 2001  (SE)  .................. 0102069-2
Nov. 30, 2001  (SE)  .................. 0104049-2
May 31, 2002  (SE)  .................. 0201660-8

(51) Int. Cl.
*A61K 3/397*  (2006.01)

(52) U.S. Cl. .............. 514/210.02; 514/210.17; 514/772; 514/777; 514/780; 548/952; 548/953

(58) Field of Classification Search ................ None
See application file for complete search history.

(56) References Cited

U.S. PATENT DOCUMENTS

| 4,346,078 A | | 8/1982 | Bajusz et al. ............ 514/19 |
| 4,703,036 A | | 10/1987 | Bajusz et al. |
| 4,792,452 A | * | 12/1988 | Howard et al. ........... 424/475 |
| 5,053,416 A | * | 10/1991 | Toja et al. ............... 514/340 |
| 5,260,307 A | | 11/1993 | Ackermann et al. |
| 5,393,760 A | | 2/1995 | Ackermann et al. |

(Continued)

FOREIGN PATENT DOCUMENTS

EP        0185390        10/1991

(Continued)

OTHER PUBLICATIONS

Talukdar et al. "In vivo evaluation of xanthan gum as a potential excipient for oral controlled-release matrix tablet formulation" International Journal of Pharmaceutics 169(1):105-113 (1998).

(Continued)

*Primary Examiner*—Eric E. Silverman
(74) *Attorney, Agent, or Firm*—Morgan, Lewis & Bockius LLP

(57) ABSTRACT

An oral pharmaceutical formulation comprising iota-carrageenan, one or more neutral gelling polymers and a basic pharmaceutically active ingredient; which formulation inhibits the release of the basic pharmaceutically active ingredient from the formulation at acidic pH; a process for the manufacture of said formulation; and the use of said formulation in medicine.

7 Claims, 6 Drawing Sheets

U.S. PATENT DOCUMENTS

Figure 1:
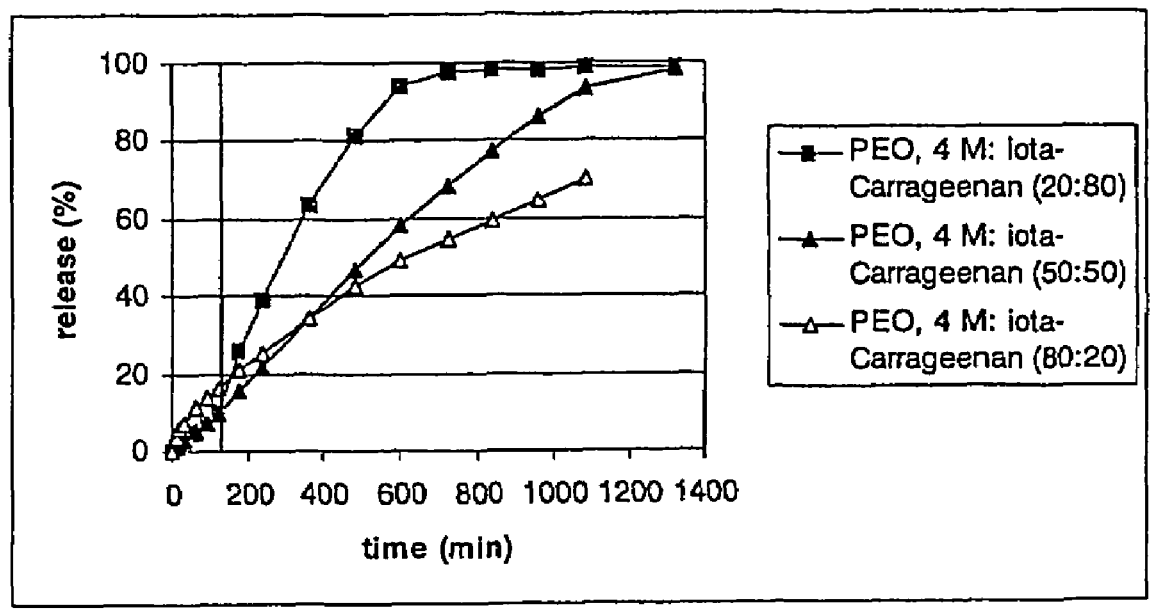

| | | | |
|---|---|---|---|
| 5,405,854 A | 4/1995 | Ackermann et al. | |
| 5,498,724 A | 3/1996 | Nystrom et al. | 548/375.1 |
| 5,532,232 A | 7/1996 | Ackermann et al. | |
| 5,559,232 A | 9/1996 | Ackermann et al. | 544/121 |
| 5,578,594 A | 11/1996 | Ackermann et al. | |
| 5,583,133 A | 12/1996 | Ackermann et al. | |
| 5,595,999 A | 1/1997 | Ackermann et al. | |
| 5,602,253 A | 2/1997 | Antonsson et al. | 544/330 |
| 5,659,071 A | 8/1997 | Nystrom et al. | 560/159 |
| 5,677,448 A | 10/1997 | Ackermann et al. | |
| 5,705,487 A | 1/1998 | Schacht et al. | 514/19 |
| 5,707,966 A | 1/1998 | Schacht et al. | 514/19 |
| 5,710,130 A | 1/1998 | Schacht et al. | 514/19 |
| 5,723,444 A | 3/1998 | Antonsson et al. | 514/19 |
| 5,744,487 A | 4/1998 | Ohshima et al. | 514/326 |
| 5,763,436 A | 6/1998 | Ackermann et al. | |
| 5,763,604 A | 6/1998 | Ackermann et al. | |
| 5,780,631 A | 7/1998 | Antonsson et al. | 546/1 |
| 5,783,563 A | 7/1998 | Antonsson et al. | 514/19 |
| 5,856,307 A | 1/1999 | Antonsson et al. | 514/18 |
| 5,939,392 A | 8/1999 | Antonsson et al. | 514/18 |
| 5,965,692 A | 10/1999 | Gustafsson et al. | 530/300 |
| 6,030,972 A | 2/2000 | Bohm et al. | 514/257 |
| 6,034,104 A | 3/2000 | Klimkowski et al. | |
| 6,051,568 A | 4/2000 | Gustafsson et al. | 514/210.17 |
| 6,083,532 A | 7/2000 | Zhang et al. | |
| 6,221,898 B1 | 4/2001 | Antonsson | 514/445 |
| 6,225,287 B1 | 5/2001 | Edvardsson et al. | 514/19 |
| 6,255,301 B1 | 7/2001 | Gustafsson et al. | |
| 6,262,028 B1 | 7/2001 | Antonsson et al. | 514/19 |
| 6,265,397 B1 | 7/2001 | Karlsson et al. | 514/210.17 |
| 6,287,599 B1 | 9/2001 | Burnside et al. | |
| 6,337,343 B1 | 1/2002 | Gustafsson et al. | |
| 6,337,346 B1 | 1/2002 | Lee et al. | |
| 6,337,394 B2 | 1/2002 | Karlsson et al. | |
| 6,433,186 B1 | 8/2002 | Inghardt et al. | |
| 6,440,937 B1 | 8/2002 | Baucke et al. | 514/19 |
| 6,440,939 B2 | 8/2002 | Edvardsson et al. | 514/19 |
| 6,444,817 B1 | 9/2002 | Bohm et al. | 544/334 |
| 6,455,671 B1 | 9/2002 | Bohm et al. | 530/331 |
| 6,479,078 B1 | 11/2002 | Hedstrom et al. | 424/489 |
| 6,521,253 B1 | 2/2003 | Forsman et al. | 424/464 |
| 6,576,245 B1 | 6/2003 | Lundgren et al. | 424/400 |
| 6,576,657 B2 | 6/2003 | Karlsson et al. | 514/423 |
| 6,599,894 B1 | 7/2003 | Inghardt et al. | 514/210.02 |
| 6,617,320 B2 | 9/2003 | Gustafsson et al. | |
| 6,660,279 B2 | 12/2003 | Lundgren et al. | 424/400 |
| 6,716,834 B2 | 4/2004 | Andersson et al. | 514/210.02 |
| 6,750,243 B1 | 6/2004 | Inghardt et al. | 514/422 |
| 6,811,794 B2 | 11/2004 | Burnside et al. | |
| 6,838,478 B2 | 1/2005 | Gustafsson et al. | |
| 6,875,446 B2 | 4/2005 | Forsman et al. | 424/464 |
| 6,888,007 B2 | 5/2005 | Edvardsson et al. | 548/953 |
| 6,921,758 B2 | 7/2005 | Gustafsson et al. | 514/210.17 |
| 6,984,627 B1 | 1/2006 | Antonsson et al. | 514/19 |
| 6,998,136 B2 | 2/2006 | Lundgren et al. | 424/422 |
| 7,056,907 B2 | 6/2006 | Inghardt et al. | 514/210.02 |
| 7,129,233 B2 * | 10/2006 | Inghardt et al. | 514/210.02 |
| 7,202,236 B2 | 4/2007 | Magnusson et al. | |
| 7,273,858 B2 | 9/2007 | Ahlqvist et al. | |
| 2003/0004308 A1 | 1/2003 | Bohm et al. | |
| 2004/0019033 A1 | 1/2004 | Inghardt et al. | 514/210.17 |
| 2004/0242492 A1 | 12/2004 | Inghardt et al. | 514/19 |
| 2005/0171083 A1 | 8/2005 | Magnusson et al. | |
| 2006/0014734 A1 | 1/2006 | Alami et al. | |
| 2006/0111553 A1 | 5/2006 | Boehm et al. | |
| 2007/0202174 A1 | 8/2007 | Inghardt et al. | |
| 2007/0218136 A1 | 9/2007 | Inghardt et al. | |
| 2008/0050437 A1 | 2/2008 | Magnusson et al. | |
| 2008/0090800 A1 | 4/2008 | Inghardt et al. | |
| 2008/0269176 A1 | 10/2008 | Ahlqvist et al. | |
| 2008/0287413 A1 | 11/2008 | Ymen et al. | |
| 2008/0293965 A1 | 11/2008 | Bosson | |
| 2008/0312457 A1 | 12/2008 | Blixt et al. | |
| 2008/0319206 A1 | 12/2008 | Al-Saffar et al. | |

FOREIGN PATENT DOCUMENTS

| | | |
|---|---|---|
| EP | 0526877 | 2/1993 |
| EP | 0293881 | 3/1993 |
| EP | 0530167 | 3/1993 |
| EP | 0539059 | 4/1993 |
| EP | 0195212 | 11/1993 |
| EP | 0468231 | 9/1994 |
| EP | 0641779 | 3/1995 |
| EP | 0648780 | 4/1995 |
| EP | 0362002 | 7/1995 |
| EP | 0686642 | 12/1995 |
| EP | 0364344 | 5/1998 |
| EP | 0542525 | 7/1998 |
| EP | 0559046 | 7/2001 |
| EP | 0669317 | 9/2002 |
| EP | 0773955 | 4/2003 |
| EP | 0672658 | 9/2003 |
| JP | 57149217 | 9/1982 |
| WO | WO 93/11152 | 6/1993 |
| WO | WO 93/18060 | 9/1993 |
| WO | WO 94/29269 | 12/1994 |
| WO | WO 94/29336 | 12/1994 |
| WO | WO 95/23609 | 9/1995 |
| WO | WO 95/35309 | 12/1995 |
| WO | WO 96/03374 | 2/1996 |
| WO | WO 96/25426 | 8/1996 |
| WO | WO 96/26717 | 9/1996 |
| WO | WO 96/31504 | 10/1996 |
| WO | WO 96/32110 | 10/1996 |
| WO | WO 97/02284 | 1/1997 |
| WO | WO 97/23499 | 7/1997 |
| WO | WO 97/39770 | 10/1997 |
| WO | WO 97/46577 | 12/1997 |
| WO | WO 97/49404 | 12/1997 |
| WO | WO 98/01422 | 1/1998 |
| WO | WO 98/06740 | 2/1998 |
| WO | WO 98/16252 | 4/1998 |
| WO | WO 98/57932 | 12/1998 |
| WO | WO 99/21586 | 5/1999 |
| WO | WO 99/27913 | 6/1999 |
| WO | WO 99/29305 | 6/1999 |
| WO | WO 99/29664 | 6/1999 |
| WO | WO 99/39698 | 8/1999 |
| WO | WO 00/12043 | 3/2000 |
| WO | WO 00/13671 | 3/2000 |
| WO | WO 00/13710 | 3/2000 |
| WO | WO 00/14110 | 3/2000 |
| WO | WO 00/18352 | 4/2000 |
| WO | WO 00/35869 | 6/2000 |
| WO | WO 00/42059 | 7/2000 |
| WO | WO 01/02426 | 1/2001 |
| WO | WO 01/87879 | 11/2001 |
| WO | WO 02/14270 | 2/2002 |
| WO | WO 02/19990 | 3/2002 |
| WO | WO 02/44145 | 6/2002 |
| WO | WO 03/000293 | 1/2003 |
| WO | WO 03/018551 | 3/2003 |
| WO | WO 03/090723 | 11/2003 |
| WO | WO 03/101423 | 12/2003 |
| WO | WO 03/101424 | 12/2003 |
| WO | WO 03/101957 | 12/2003 |
| WO | WO 2005/054168 | 6/2005 |
| WO | WO 2006/090153 | 8/2006 |
| WO | WO 2006/125964 | 11/2006 |

| WO | WO 2008/068475 | 6/2008 |

OTHER PUBLICATIONS

Baveja et al. "Zero-order release hydrophilic matrix tablets of beta-adrenergic blockers" International Journal of Pharmaceutics 39:39-45 (1987).

Bonferoni et al. "On the employment of lambda-carrageenan in a matrix system. II. Lambda-Carrageenan and hydroxypropylmethylcellulose mixtures" J. Controlled Release 30:175-182 (1994).

Ham-Yong Park et al. "Effect of pH on Drug Release From Polysaccharide Tablets" Drug Delivery 5:13-18 (1998).

Picker "The use of carrageenan in mixture with microcrystalline cellulose and its functionality for making tablets" European J. Pharmaceutics and Biopharmaceutics 48(1):27-36 (1999).

Gupta et al. "Controlled-release tablets from carrageenans: effect of formulation, storage and dissolution factors" Eur. J. Pharm. Biopharm., 51(3):241-248 (2001).

Talukdar et al. "Comparative study on xanthan gum and hydroxypropylmethyl cellulose as matrices for controlled-release drug delivery I. Compaction and in vitro drug release behaviour" International Journal of Pharmaceutics, 129(2):233-241 (1996).

Berge et al. "Pharmaceutical Salts" J. of Pharmaceutical Sciences 66(1):1-19 (1977).

CAS RN 159776-70-2 Dec. 1994.

CAS RN 192939-72-3 Aug. 1997.

CAS RN 30318-53-4 Nov. 2000.

\* cited by examiner

PHARMACEUTICAL FORMULATION

RELATED APPLICATIONS

This application is a national stage filing under 35 U.S.C. 371 of International Application PCT/SEO2/01217, filed Jun. 19, 2002, which claims priority from Sweden Application Nos. 0102069-2, filed Jun. 21, 2001, 0104049-2, filed Nov. 30, 2001, and 0201660-8, filed May 31, 2002, the specifications of each of which are incorporated by reference herein. International Application PCT/SE02/01217 was published under PCT Article 21(2) in English.

The present invention concerns a new oral pharmaceutical formulation, comprising a basic pharmaceutically active ingredient having pH-dependent solubility, which inhibits the release of the basic pharmaceutical active ingredient from the formulation at acidic pH (preferably below pH 3) and preferably provides substantially pH-independent controlled-release of the pharmaceutically active ingredient over the broad pH range in the gastrointestinal tract; a process for the manufacture of said formulation; and to the use of said formulation in medicine.

Effective controlled-release pharmaceutical formulations are desirable pharmaceutical products, as these allow: optimization of drug therapy; and an opportunity both to decrease frequency of dosage and to minimize undesirable side effects. However, the design of such controlled-release systems is not a simple matter, especially when the drug formulation is intended for oral administration and has to pass through the gastrointestinal tract, which exhibits, among other characteristics, a large variation in pH along its length.

Many drugs showing basic properties ionize at low pH and become significantly more soluble in this pH region compared to a more neutral environment. This manifestation of pH-dependent solubility in the gastrointestinal tract can result in variable drug release profiles, with parallel in-vivo bioavailability problems.

Several attempts to overcome the problem of pH-dependent solubility of basic drugs have been described. These strategies include the use of an enteric polymer, which is insoluble at low pH, to retard drug release in low pH environments [see, for example, U.S. Pat. No. 4,968,508, and A. Streubel et al. J. Controlled Release, 67, 101-110 (2000)], or the incorporation of a low molecular weight organic acid to create an acidic micro-environmental pH inside the formulation matrix, thus keeping the solubility of the drug constant [see, for example, K. E. Gabr., Eur. J. Pharm. Biopharm., 38(6), 199-202 (1992), and V. K. Thoma and Th. Zimmer, Pharm. Ind. 51(1), 98-101 (1989)]. The incorporation of an anionic polymer (for example sodium alginate) showing pH-dependent solubility in a drug formulation which also comprises a neutral polymer, gave insoluble gelling properties at low pH, resulting in a strong diffusional barrier which was theorized to be the main mechanism retarding drug release at low pH. [U.S. Pat. No. 4,792,452; and P. Timmins et al. Pharmaceutical Development and Technology, 2(1), 25-31 (1997)]. Other methods have involved employing charged polymers to influence drug release by either ionically interacting with the drug [see C. Caramella et al. Pharm. Res. 14(11), 531 (1997), H. Y. Park et al. Drug Delivery, 5 13-18 (1998), N. Caram-Lelham, Ph.D. thesis, Uppsala University (1996)] or by influencing the gelling and swelling properties of these polymers [see K. M. Picker, Drug Dev. and Ind. Pharmacy, 25(3) 339-346 (1999)]. The formulations used here were generally based on one type of polymer.

Baveja et al, Int J Pharmaceutics 39, 39-45 (1987) discloses that when a nonionic polymer (HPMC) is mixed with an anionic polymer (NaCMC) release is retarded. Ranga Rao et al, Drug Dev Ind Pharmacy, 14, 2299 (1988) disclose mixtures of methyl cellulose and NaCMC to give different release profiles. Mixtures of lambda-carrageenan and active ingredient are disclosed in WO 99/21586.

Combinations of strategies to give a pH-independent release profile have been reported [see WO 96/26717, WO 99/29305 and WO 99/39698]. All three of these disclose a three component matrix formulation comprising three polymers with typically different aqueous solubility and swelling properties, the composition of which may be varied, with adjustment of these properties, to give adjustable release rates. Two of the components involve a gelling polymer with significant pH-dependent solubility such as sodium alginate, and a gelling polymer with low or insignificant pH-dependent solubility, such as hydroxy propyl methyl cellulose (HPMC) or polyethylene oxide. The third component involves either an enteric coating polymer, such as methacrylic acid copolymer (WO 96/26717); EUDRAGIT® L or S, which are specific types of methacrylic acid polymers, (WO 99/29305); or a water insoluble polymer, such as ethyl cellulose (WO 99/39698). However, these strategies, have not, in general, specifically targeted basic drugs, and have depended on enteric coat-type or water insoluble polymers, such as a methacrylic acid polymer, or a pH-dependent gelling polymer, such as sodium alginate, to retard drug release at low pH environments, at least in some part.

The present invention provides an oral pharmaceutical formulation comprising iota-carrageenan, one or more neutral gelling polymers and a basic pharmaceutically active ingredient; which formulation inhibits the release of the basic pharmaceutically active ingredient from the formulation at acidic pH (preferably below pH 3; especially about pH 1).

Substantially pH independent release means that the release rate is significantly redarded at pH 1 and slightly increased or unaffected at pH 6.8 so that the amount of basic pharmaceutically active ingredient released at any one time becomes less pH dependent.

The present invention further provides an oral pharmaceutical formulation comprising iota-carrageenan, one or more neutral gelling polymers and a basic pharmaceutically active ingredient.

Iota-carrageenan is, preferably, present in the formulation of the invention at a level of more that 15% by weight. The iota-carrageenan is preferably of natural origin. One type of pharmaceutical grade iota-carrageenan (available from FMC Biopolymer) has a viscosity of not less than 5 centipoise (cps), preferably in the range 5-10 cps (for a 1.5% solution warmed to 82° C., after which the viscosity is measured at 75° C. with a Brookfield LV viscometer fitted with a #1 spindle running at a speed of 30 rpm). A type of technical grade iota-carrageenan (available from Fluka Biochemica) preferably has a viscosity of not less than 14 mPa·s, for a 0.3% aqueous solution warmed to 20° C., after which the viscosity is measured using a fallingball viscometer, of type Haake, used together with a Lauda thermostat C3 and Hakke Mess-System III, and using gold-coated stainless steel balls of density 7.8 g/cm$^3$.

The neutral gelling polymer is a single, or a mixture of more than one, neutral erodable polymer(s) having gelling properties and having substantially pH-independent solubility. The neutral gelling polymer is, preferably, present in the formulation at a level of more that 10% but preferably more than 20% by weight. {"Erodable" and "erosion" refer to dissolution or disintegration either alone or in combination.

Dissolution can be enhanced by mixing and disintegration can be enhanced by mechanical interaction with solid matter.}

Suitable neutral gelling polymers include polyethylene oxide (PEO), derivatives and members of the PEO family (for example, polyethylene glycol (PEG), preferably existing naturally in the solid state, of suitable molecular weight or viscosity). Thus the neutral gelling polymer is, for example, a polyethylene oxide or polyethylene glycol.

If used as a single neutral gelling polymer, a PEO preferably has a MW of ≧4 million (4M) (for example a MW of 4 to 8 million), corresponding to an aqueous solution viscosity range of 1650-5500 mPa·s (or 1650-5500 cps; measured for a 1% aqueous solution at 25° C., using a Brookfield RVF viscometer, with No. 2 spindle, at 2 rpm). Other examples of suitable PEOs include a PEO of MW around 5 million (5M), corresponding to an aqueous solution viscosity range of 5500-7500 mPa·s, or a PEO MW around 8 million (8M), corresponding to an aqueous solution viscosity range of 10000-15000 mPa·s. This range covers the value for typical solution viscosity (in cps) measured at 25° C., quoted for this polymer, in the USP 24/NF 19, 2000 edition, pp. 2285-2286. Thus, PEO can have a MW of 4-8 million.

If PEG is used as a single neutral gelling polymer it preferably has a high molecular weight, for example, a MW of around 20000, corresponding to a viscosity range of 2700-3500 mPa·s (or 2700-3500 cps), measured using a 50% aqueous solution (w/w) at 20° C., using a capillary viscometer (Ubbelohde or equivalent). [Ref: European Pharmacopoeia $3^{rd}$ Ed., 2000, Supplement, pp. 908-909.]

Other suitable gelling polymers include cellulose derivatives such as hydroxypropylmethyl cellulose (HPMC) or bydroxyethylcellulose (HEC) (but preferably HPMC with suitably high viscosities (for example "HPMC 10000 cps", "HPMC 15000 cps", "HEC type HH" or "HEC type H"). When used as a single neutral polymer, hydroxypropylmethyl cellulose polymers like "HPMC 10000 cps" and "HPMC 15000 cps" have, respectively, apparent viscosities of 7500-14000 mPa·s (or 7500-14000 cps), and 11250-21000 mPa·s (or 11250-21000 cps), when measured at 20° C. with a 2% (w/w) aqueous solution, calculated with reference to the dried substance, using a capillary viscometer (Ubbelohde or equivalent). One type of hydroxyethylcellulose polymer, for example, "Natrosol 250 Pharma, type HH", from Hercules Incorporated (Aqualon), shows typically a Brookfield viscosity of about 20,000 mPa·s using a Brookfield Synchro-Lectric Model LVF instrument, at the conditions 1% solution concentration, spindle no. 4, spindle speed 30 rpm, factor 200, 25° C. (See Natrosol Physical and Chemical Properties booklet, 33.007-E6 (1993), p. 21).

When a mixture of neutral gelling polymers is used the mixture can, for example, comprise a mixture or blend of two or more PEOs, two or more HPMCs, a PEO and an HPMC or a PEO and a PEG. For example, a PEO of MW 4, 5 or 8 million could be blended with a PEO of MW 1 million, a PEO of MW 400,000, a PEO of MW 100,000 or a PEG of MW 6000.

Alternatively, a neutral gelling polymer (for example a PEO) can be used in combination with a non-gelling neutral polymer (such as a low MW PEG, for example a PEG having a MW below 10000). Examples of low MW PEGs in such a combination include a PEG of MW 8000 (corresponding to a viscosity range of 260-510 mPa·s) or a PEG of MW 6000 (corresponding to a viscosity range of 200-270 mPa·s).

A mixture or blend of two or more HPMC grades can include both lower viscosity (non-gelling) and higher viscosity (gelling) grades. For example, "HPMC 50 cps", "HPMC 15 cps" and "HPMC 6 cps", having, respectively, apparent viscosities of 40-60 mPa·s, 11.3-21.0 mPa·s and 4.8-7.2 mPa·s, according to the method earlier defined above, can be used as blends with "HPMC 10000 cps" or "HPMC 15000 cps".

A blend of two or more polymers of the same kind but of different MWs gives better erosion control when the formulation of the invention is in tablet form. When used alone or in a mixture, the higher the MW of PEO used, the less of this polymer is required to make a formulation according to the invention.

The exact formulation of the invention is dependent on the molecular weight and molecular weight distribution of the gelling polymer chosen, as well as the quality of each of the polymers employed.

In one aspect of the invention the neutral gelling polymer is a PEO of MW of about 4 million or more, a PEG of MW of about 20000 or more, or a cellulose derivative having an apparent viscosity of about 7500 cps or more (measured as above).

The ratio of neutral gelling polymer (for example PEO, PEG or HPMC; especially PEO or HPMC; or mixture thereof with each other or of 2 or more PEO or HPMC) to iota-carrageenan is preferably in the range 20:80 to 80:20 (especially about 40:60 to 60:40, for example about 50:50).

Basic pharmaceutically active ingredients have one or more basic groups having a pKa preferably from 1 to 12 (for example from 1 to 10 (especially from 1 to 7)), and optionally also having one or more basic groups having a pKa of more than 10. Thus, the basic pharmaceutically active ingredient may possess one or more pKa values but at least one is, preferably, from 1 to 12 (for example from 1 to 10 (especially from 1 to 7)). Examples of basic groups in these basic pharmaceutically active ingredients having pKa's of from 1 to 12 (for example from 1 to 10) include hydroxyamidines, secondary or tertiary amines, or primary and secondary amides.

Suitable basic pharmaceutically active ingredients preferably have low to medium aqueous solubility (for example an aqueous solubility of up to 50 mg/ml (especially 0.001 to 20 mg/ml) at 25° C. and at pH 7.0), and are positively charged with one or more positive charges (depending on the number and pKa of the basic groups in the pharmaceutically active ingredient) at low pH (for example pH 1 to 6 (especially pH 1 to 2)).

A suitable basic pharmaceutically active ingredient is, for example, a compound having cardiovascular activity (such as a peptide, or peptide like, thrombin inhibitor). Peptide thrombin inhibitors have a molecular weight below 1000, have 1, 2, 3 or 4 peptide linkages and show pH dependent solubility. They include the peptide thrombin inhibitors (and prodrugs therefore) described generically, and more specifically, in the review paper by Claesson in Blood Coagul. Fibrin. 5. 411, (1994), as well as those disclosed in U.S. Pat. No. 4,346,078; International Patent Applications WO 97/23499, WO 97/02284, WO97/46577, WO 98/01422, WO 93/05069, WO93/11152, WO 95/23609, WO95/35309, WO 96/25426, WO 94/29336, WO 93/18060 and WO 95/01168; and European Patent Publication nos. 623 596, 648 780, 468 231, 559 046, 641 779, 185 390, 526 877, 542 525, 195 212, 362 002, 364 344, 530 167, 293 881, 686 642, 669 317 and 601 459. Peptide thrombin inhibitors (or prodrugs therefore) especially include inogatran, melagatran {HOOC—$CH_2$—RCgl-Aze-Pab-H; Glycine, N-[2-[2-[[[[4 (aminoiminomethyl)phenyl]-methyl]amino]carbonyl]-1-azetidinyl]-1-cyclohexyl-2-oxoethyl]-, [2R-[2S]]—)} and H376/95 {ximelagatran; $EtO_2C$—$CH_2$—RCgl-Aze-Pab-OH; see Example 17 of WO 97/23499; Glycine, N-[1-cyclohexyl-2-[2-[[[[4-[(hydroxyimino)aminomethyl]-phenyl]methyl]amino]carbonyl]-1-azetidinyl]-2-oxoethyl]-, ethyl ester, [S—(R*, S*)]—}.

In another aspect peptide thrombin inhibitors (or prodrugs therefore) include inogatran, melagatran, H376/95, Ph(3-Cl)(5-OCH$_2$CH$_2$F)—(R)CH(OH)C(O)-Aze-Pab(OMe) and Ph(3-Cl)(5-OCHF$_2$)—(R)CH(OH)C(O)-Aze-Pab(OMe).

In another aspect the present invention provides a formulation as herein described wherein the basic, pharmaceutically active ingredient is:

Ph(3-Cl)(5-OCHF$_2$)—(R)CH(OH)C(O)—(S)Aze-Pab(OMe) {Compound A};

Ph(3-Cl)(5-OCHF$_2$)—(R)CH(OH)C(O)—(S)Aze-Pab(2,6-diF)(OMe) {Compound D};

Ph(3-Cl)(5-OCH$_2$CH$_2$F)—(R)CH(OH)C(O)—(S)Aze-Pab(OMe) {Compound E};

Ph(3-Cl)(5-OCHF$_2$)—(R)CH(OH)C(O)—(S)Aze-Pab(OH) {Compound F};

Ph(3-Cl)(5-OCHF$_2$)—(R)CH(OH)C(O)—(S)Aze-Pab(2,6-diF)(OH) {Compound G};

Ph(3-Cl)(5-OCH$_2$CH$_2$F)—(R)CH(OH)C(O)—(S)Aze-Pab(OH) {Compound H}.

Compound G can be prepared by methods similar to those described below for the preparation of Compounds F and H.

In another aspect the present invention provides a pharmaceutical formulation wherein the basic, pharmaceutically active ingredient is:

1. 4-({3-[7-(3,3-dimethyl-2-oxobutyl)-9-oxa-3,7-diazabicyclo[3.3.1]non-3-yl]propyl}amino)benzonitrile (which compound is referred to hereinafter as Compound B);
2. tert-butyl 2-{7-[3-(4-cyanoanilino)propyl]-9-oxa-3,7-diazabicyclo-[3.3.1]non-3-yl}ethylcarbamate;
3. tert-butyl 2-{7-[4-(4-cyanophenyl)butyl]-9-oxa-3,7-diazabicyclo-[3.3.1]non-3-yl}ethylcarbamate; or
4. tert-butyl 2-{7-[(2S)-3-(4-cyanophenoxy)-2-hydroxypropyl]-9-oxa-3,7-diazabicyclo[3.3.1]non-3-yl}ethylcarbamate (which compound is referred to hereinafter as Compound C);

these compounds having been described in WO 01/28992.

In a further aspect the basic pharmaceutically active ingredient is metoprolol or a salt thereof (such as a succinate or tartrate thereof).

The formulation of the present invention can include: a processing additive, stabiliser, plasticiser, colourant, lubricant (such as sodium stearyl fumarate), binder, filler or surfactant, or other excipient normally used in a pharmaceutical preparation.

In one particular aspect the formulation of the present invention includes a lubricant (such as sodium stearyl fumarate).

In another aspect of the present invention the molar ratio of iota-carrageenan to basic pharmaceutically active ingredient is in the range 3:1 to 1:3.

In a further aspect the pharmaceutical formulation of the present invention comprises 15-80% iota-carrageenan.

In another aspect the pharmaceutical formulation of the present invention comprises 15-80% of one or more neutral gelling polymers.

In a further aspect the pharmaceutical formulation of the present invention comprises 1-50% of a basic pharmaceutically active ingredient.

In a still further aspect the pharmaceutical formulation of the present invention comprises 0-10% (especially 1-10%) of a processing additive, stabiliser, plasticiser, colourant, lubricant, binder or filler, or other excipient normally used in a pharmaceutical preparation.

The mechanism behind the inhibition of the release of the basic pharmaceutical active ingredient from the formulation at acidic pH (especially the substantially pH-independent controlled release) is thought to be as follows. At low pH, the basic pharmaceutically active ingredient drug would be expected to have a relatively high solubility as it is in a strongly-ionized state, and, therefore, would be expected to show a fast release profile from any neutral matrix. It is theorised that, at acidic pH and in the presence of iota-carrageenan, an ionic attraction exists between the negatively charged iota-carrageenan and the positively charged drug, which retards drug release and thus contributes towards a more constant release profile. At higher pH, when the pharmaceutical drug is less strongly ionized, or not ionised at all, and, therefore, would be expected to show a slow release profile from any neutral matrix, it is theorised that the ionic interaction proposed above is also less significant and the release profile is controlled predominantly by the combined swelling, gelling and erosion profiles of the neutral gelling polymer/s, and the anionic polymer, iota-carrageenan, used in the formulation.

The final swelling, gelling and erosion properties of the formulation of the invention are related to properties like the molecular weight, and molecular weight distribution of the gelling polymer/s, and the anionic polymer, and also related to the pH-dependent hydrolysis rate of the anionic polymer. Thus, different release rates for the basic pharmaceutically active ingredient may be obtained by adjusting the nature (for example the molecular weight or molecular weight distribution) of the gelling polymer, the amount of iota-carrageenan present in the formulation and/or the ratio of gelling polymer to iota-carrageenan.

The formulation of the present invention can be presented as a solid dosage form (such as a tablet, capsule, pellet or powder dispersed in a suitable container, or in the form of a multiple formulation (such as coated pellets administered in a tablet, capsule or sachet)).

In one aspect the invention provides a tablet comprising 20-500 mg (especially 40-60 mg) of basic pharmaceutically active ingredient (such as H376/95; or Compound A, B or C).

When the pharmaceutical formulation of the present invention is presented in a tablet the tablet is preferably made such that all the basic pharmaceutically active ingredient is released, in ionised or unionised form depending on the pH of each part of the gastrointestinal tract, over a period of about 20 hours, for example 18-22 hours (alternatively for 20 to 26 hours).

In a still further aspect there is provided a process for preparing a formulation of the present invention comprising mixing iota-carrageenan, one or more neutral gelling polymers and a basic pharmaceutically active ingredient and, optionally compressing said mixture (preferably in the presence of a lubricant {such as sodium stearyl fumarate, sold under the trade name PRUV™}) to form a tablet.

A tablet formulation can be prepared, for example, by a direct compression or a wet granulation technique.

For the direct compression technique a basic pharmaceutically active ingredient is thoroughly mixed with a gelling polymer and iota-carrageenan and additional excipients as needed. A lubricant (such as sodium stearyl fumarate) is sieved and added to the iota-carrageen mixture followed by further mixing. The resulting mixture is then compressed into tablets.

For the wet granulation technique a basic pharmaceutically active ingredient is thoroughly mixed with a gelling polymer and iota-carrageenan. The resulting mixture may then be moistened with:

a solution of a suitable binder (such as polyvinylpyrolidone (PVP) dissolved in a suitable solvent (such as ethanol or water); or, a suitable solvent (such as ethanol or water); and the resulting blend is granulated using a standard or modified granulation procedures (such as spray-granulation). After drying the resulting granulate (for example in an oven at a suitable temperature (such as about 50° C.) for a suitable period (such as 20-24 hours) the granulate is milled (for example dry- or wet-milled), mixed with a lubricant (such as sodium stearyl fumarate, magnesium stearate or talc) and the resulting composition is compressed into tablets. The dried granulate could be used to fill capsules (such as capsules made of gelatin).

In another aspect the present invention provides a process for preparing a formulation as hereinbefore described.

The thrombin active compounds and their prodrugs can be used for the treatment and/or prophylaxis of thrombosis and hypercoagulability in blood and/or tissues of animals including man. It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis, as well as coagulation syndromes (for example disseminated intravascular coagulation (DIC)) and vascular injury in general (for example due to surgery).

In a further aspect the present invention provides a formulation as hereinbefore described for use in therapy (both curative and prophylactic) for example as a medicament (such as a medicament for cardiovascular disorders, for example thromboembolism).

A formulation of the invention useful in the manufacture of a medicament for use in therapy.

In another aspect the present invention provides a method of treating a cardiovascular disorder (for example thromboembolism) in a warm blooded animal suffering from, or at risk of, said disorder, which comprises administering to an animal in need of such treatment a therapeutically effective amount of a composition of the invention.

Certain peptide thrombin inhibitors, or prodrugs thereof, can be prepared by the methodologies described below.

General Procedures

TLC was performed on silica gel. Chiral HPLC analysis was performed using a 46 mm×250 mm Chiralcel OD column with a 5 cm guard column. The column temperature was maintained at 35° C. A flow rate of 1.0 mL/min was used. A Gilson 115 UV detector at 228 nm was used. The mobile phase consisted of hexanes, ethanol and trifluroacetic acid and the appropriate ratios are listed for each compound. Typically, the product was dissolved in a minimal amount of ethanol and this was diluted with the mobile phase.

In the preparations below, LC-MS/MS was performed using a HP-1100 instrument equipped with a CTC-PAL injector and a 5 Tm, 4×100 mm ThermoQuest, Hypersil BDS-C18 column. An API-3000 (Sciex) MS detector was used. The flow rate was 1.2 mL/min and the mobile phase (gradient) consisted of 10-90% acetonitrile with 90-10% of 4 mM aq. ammonium acetate, both containing 0.2% formic acid. Otherwise, low resolution mass spectra (LRMS) were recorded using a Micromass ZQ spectrometer in ESI posneg switching ion mode (mass range m/z 100-800); and high resolution mass spectra (HRMS) were recorded using a Micromass LCT spectrometer in ES negative ionization mode (mass range m/z 100-1000) with Leucine Enkephalin ($C_{28}H_{37}N_5O_7$) as internal mass standard.

$^1$H NMR spectra were recorded using tetramethylsilane as the internal standard.

Preparation of Ph(3-Cl)(5-OCHF$_2$)—(R)CH(OH)C(O)—(S) Aze-Pab(OMe) {Compound A}

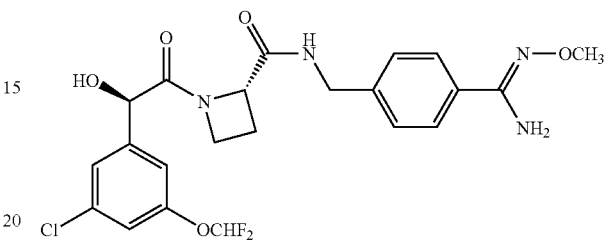

(i) 3-Chloro-5-methoxybenzaldehyde 3,5-Dichloroanisole (74.0 g, 419 mmol) in THF (200 mL) was added dropwise to magnesium metal (14.2 g, 585 mmol, pre-washed with 0.5 N HCl) in THF (100 mL) at 25° C. After the addition, 1,2-dibromoethane (3.9 g, 20.8 mmol) was added dropwise. The resultant dark brown mixture was heated at reflux for 3 h. The mixture was cooled to 0° C., and N,N-dimethylformamide (60 mL) was added in one portion. The mixture was partitioned with diethyl ether (3×400 mL) and 6N HCl (500 mL). The combined organic extracts were washed with brine (300 mL), dried (Na$_2$SO$_4$), filtered and concentrated in vacuo to give an oil. Flash chromatography (2×) on silica gel eluting with Hex:EtOAc (4:1) afforded the sub-title compound (38.9 g, 54%) as a yellow oil.

$^1$H NMR (300 MHz, CDCl$_3$) δ 9.90 (s, 1H), 7.53 (s, 1H), 7.38 (s, 1H), 7.15 (s, 1H), 3.87 (s, 3H).

(ii) 3-Chloro-5-hydroxybenzaldehyde

A solution of 3-chloro-5-methoxybenzaldehyde (22.8 g, 134 mmol; see step (i) above) in CH$_2$Cl$_2$ (250 mL) was cooled to 0° C. Boron tribromide (15.8 mL, 167 mmol) was added dropwise over 15 min. After stirring, the reaction mixture for 2 h, H$_2$O (50 mL) was added slowly. The solution was then extracted with Et$_2$O (2×100 mL). The organic layers were combined, dried (Na$_2$SO$_4$), filtered and concentrated in vacuo. Flash chromatography on silica gel eluting with Hex: EtOAc (4:1) afforded the sub-title compound (5.2 g, 25%).

$^1$H NMR (300 MHz, CDCl$_3$) δ 9.85 (s, 1H), 7.35 (s, 1H), 7.20 (s, 1H), 7.10 (s, 1H), 3.68 (s, 1H)

(iii) 3-Chloro-5-difluoromethoxybenzaldehyde

A solution of 3-chloro-5-hydroxybenzaldehyde (7.5 g, 48 mmol; see step (ii) above) in 2-propanol (250 mL) and 30% KOH (100 mL) was heated to reflux. While stirring, CHClF$_2$ was bubbled into the reaction mixture for 2 h. The reaction mixture was cooled, acidified with 1N HCl and extracted with EtOAc (2×100 mL). The organics were washed with brine (100 mL), dried (Na$_2$SO$_4$), filtered and concentrated in vacuo. Flash chromatography on silica gel eluting with Hex:EtOAc (4:1) afforded the sub-title compound (4.6 g, 46%).

$^1$H NMR (300 MHz, CDCl$_3$) δ 9.95 (s, 1H), 7.72 (s, 1H), 7.52 (s, 1H), 7.40 (s, 1H), 6.60 (t, J$_{H—F}$=71.1 Hz, 1H).

(iv) Ph(3-Cl)(5-OCHF$_2$)—(R,S)CH(OTMS)CN

A solution of 3-chloro-5-difluoromethoxybenzaldehyde (4.6 g, 22.3 mmol; see step (iii) above) in CH$_2$Cl$_2$ (200 mL)

was cooled to 0° C. ZnI$_2$ (1.8 g, 5.6 mmol) and trimethylsilyl cyanide (2.8 g, 27.9 mmol) were added and the reaction mixture was allowed to warm to room temperature and stirred for 15 h. The mixture was partially concentrated in vacuo yielding the sub-title compound as a liquid, which was used directly in step (v) below without further purification or characterization.

(v) Ph(3-Cl)(5-OCHF$_2$)—(R,S)CH(OH)C(NH)OEt

Ph(3-Cl)(5-OCHF$_2$)—(R,S)CH(OTMS)CN (6.82 g, assume 22.3 mmol; see step (iv) above) was added dropwise to HCl/EtOH (500 mL). The reaction mixture was stirred 15 h, then partially concentrated in vacuo yielding the sub-title compound as a liquid, which was used in step (vi) without further purification or characterization.

(vi) Ph(3-Cl)(5-OCHF$_2$)—(R,S)CH(OH)C(O)OEt

Ph(3-Cl)(5-OCHF$_2$)—(R,S)CH(OH)C(NH)OEt (6.24 g, assume 22.3 mmol; see step (v) above) was dissolved in THF (250 mL), 0.5M H$_2$SO$_4$ (400 mL) was added and the reaction was stirred at 40° C. for 65 h, cooled and then partially concentrated in vacuo to remove most of the THF. The reaction mixture was then extracted with Et$_2$O (3×100 mL), dried (Na$_2$SO$_4$), filtered and concentrated in vacuo to afford the sub-title compound as a solid, which was used in step (vii) without further purification or characterization.

(vii) Ph(3-Cl)(5-OCHF$_2$)—(R,SCH(OH)C(O)OH

A solution of Ph(3-Cl)(5-OCHF$_2$)—(R,S)CH(OH)C(O)OEt (6.25 g, assume 22.3 mmol; see step (vi) above) in 2-propanol (175 mL) and 20% KOH (350 mL) was stirred at room temperature 15 h. The reaction was then partially concentrated in vacuo to remove most of the 2-propanol. The remaining mixture was acidified with 1M H$_2$SO$_4$, extracted with Et$_2$O (3×100 mL), dried (Na$_2$SO$_4$) and concentrated in vacuo to give a solid. Flash chromatography on silica gel eluting with CHCl$_3$:MeOH:concentrated NH$_4$OH (6:3:1) afforded the ammonium salt of the sub-title compound. The ammonium salt was then dissolved in a mixture of EtOAc (75 mL) and H$_2$O (75 mL) and acidified with 2N HCl. The organic layer was separated and washed with brine (50 mL), dried (Na$_2$SO$_4$) and concentrated in vacuo to afford the sub-title compound (3.2 g, 57% from steps (iv) to (vii)).

$^1$H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.16 (s, 1H)

(viii) Ph(3-Cl)(5-OCHF$_2$)—(R)CH(OH)C(O)OH (a) and Ph(3-Cl)(5-OCHF$_2$)—(S)CH(OAc)C(O)OH (b)

A mixture of Ph(3-Cl)(5-OCHF$_2$)—(R,S)CH(OH)C(O)OH (3.2 g, 12.7 mmol; see step (vii) above) and Lipase PS "Amano" (~2.0 g) in vinyl acetate (125 mL) and MTBE (125 mL) was heated at reflux for 48 h. The reaction mixture was cooled, filtered through Celite® and the filter cake washed with EtOAc. The filtrate was concentrated in vacuo and subjected to flash chromatography on silica gel eluting with CHCl$_3$:MeOH:concentrated NH$_4$OH (6:3:1) yielding the ammonium salts of the sub-title compounds (a) and (b). Compound (a) as a salt was dissolved in H$_2$O, acidified with 2N HCl and extracted with EtOAc. The organic layer was washed with brine, dried (Na$_2$SO$_4$), filtered and concentrated in vacuo to afford the sub-title compound (a) (1.2 g, 37%).

For sub-title compound (a)

$^1$H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.17 (s, 1H)

(ix) Ph(3-Cl)(5-OCHF$_2$)—(R)CH(OH)C(O)-Aze-Pab(Teoc)

To a solution of Ph(3-Cl)(5-OCHF$_2$)—(R)CH(OH)C(O)OH (1.1 g, 4.4 mmol; see step (viii) above) and H-Aze-Pab (Teoc) (see international patent application WO 00/42059, 2.6 g, 5.7 mmol) in DMF (50 mL) at 0° C. was added PyBOP (2.8 g, 5.3 mmol) and collidine (1.3 g, 10.6 mmol). The reaction was stirred at 0° C. for 2 h and then at room temperature for an additional 15 h. The reaction mixture was concentrated in vacuo and flash chromatographed on silica gel (3×), eluting first with CHCl$_3$:EtOH (9:1), then with EtOAc:EtOH (20:1) and finally eluting with CH$_2$Cl$_2$:CH$_3$OH (95:5) to afford the sub-title compound (1.0 g, 37‰) as a white solid.

$^1$H NMR (300 MHz, CD$_3$OD, mixture of rotamers) δ 7.79-7.85 (d, J=8.7 Hz, 2H), 7.15-7.48 (m, 5H), 6.89 and 6.91 (t, J$_{H-F}$=71.1 Hz, 1H), 5.12 and 5.20 (s, 1H), 4.75-4.85 (m, 1H), 3.97-4.55 (m, 6H), 2.10-2.75 (m, 2H), 1.05-1.15 (m, 2H), 0.09 (s, 9H)

MS (m/z) 611 (M+1)$^+$ (x) Ph(3-Cl)(5-OCHF$_2$)—(R)CH(OH)C(O)-Aze-Pab(OMe, Teoc)

Ph(3-Cl)(5-OCHF$_2$)—(R)CH(OH)C(O)-Aze-Pab(Teoc) (0.40 g, 0.65 mmol; see step (ix) above), was dissolved in 20 mL of acetonitrile and 0.50 g (6.0 mmol) of O-methyl hydroxylamine hydrochloride was added. The mixture was heated at 70° C. for 2 h. The solvent was evaporated and the residue was partitioned between water and ethyl acetate. The aqueous phase was extracted twice more with ethyl acetate and the combined organic phase was washed with water, brine, dried (Na$_2$SO$_4$), filtered and evaporated. Yield: 0.41 g (91%).

$^1$H-NMR (400 MHz; CDCl$_3$): δ 7.83 (bt, 1H), 7.57 (bs, 1H), 7.47 (d, 2H), 7.30 (d, 2H), 7.20 (m, 1H), 7.14 (m, 1H), 7.01 (m, 1H), 6.53 (t, 1H), 4.89 (s, 1H), 4.87 (m, 1H), 4.47 (m, 2H), 4.4-4.2 (b, 1H), 4.17-4.1 (m, 3H), 3.95 (s, 3H), 3.67 (m, 1H), 2.68 (m, 1H), 2.42 (m, 1H) 0.97 (m, 2H), 0.01 (s, 9H).

(xi) Ph(3-Cl)(5-OCHF$_2$)—(R)CH(OH)C(O)—(S)Aze-Pab(OMe)

Ph(3-Cl)(5-OCHF$_2$)—(R)CH(OH)C(O)-Aze-Pab(OMe, Teoc) (0.40 g, 0.62 mmol; see step (x) above), was dissolved in 5 mL of TFA and allowed to react for 30 min. TFA was evaporated and the residue was partitioned between ethyl acetate and NaHCO$_3$ (aq.). The aqueous phase was extracted twice more with ethyl acetate and the combined organic phase was washed with water, brine, dried (Na$_2$SO$_4$), filtered and evaporated. The product was freeze dried from water/acetonitrile. No purification was necessary. Yield: 0.28 g (85%).

$^1$H-NMR (600 MHz; CDCl$_3$): δ 7.89 (bt, 1H), 7.57 (d, 2H), 7.28 (d, 2H), 7.18 (m, 1H), 7.13 (m, 1H), 6.99 (m, 1H), 6.51 (t, 1H), 4.88 (s, 1H), 4.87 (m, 1H), 4.80 (bs, 2H), 4.48 (dd, 1H), 4.43 (dd, 1H), 4.10 (m, 1H), 3.89 (s, 3H), 3.68 (m, 1H), 2.68 (m, 1H), 2.40 (m, 1H). $^3$C-NMR (125 MHz; CDCl$_3$): (carbonyl and/or amidine carbons, rotamers) δ 172.9, 170.8, 152.7, 152.6

HRMS calculated for C$_{22}$H$_{23}$ClF$_2$N$_4$O$_5$ (M-H)$^-$495.1242. Found 495.1247.

Preparation of Compound D (Ph(3-Cl)(5-OCHF$_2$)—(R)CH(OH)C(O)—(S)Aze-Pab(2,6-diF)(OMe))

(i) 2,6-Difluoro-4[(methylsulfinyl)(methylthio)methyl]benzonitrile (Methylsulfinyl)(methylthio)methane (7.26 g, 0.0584 mol) was dissolved in 100 mL of dry THF under argon and was cooled to −78° C. Butyllithium in hexane (16 mL 1.6M, 0.0256 mol) was added dropwise with stirring. The mixture was stirred for 15 min. Meanwhile, a solution of 3,4,5-trifluorobenzonitrile (4.0 g, 0.025 mmol) in 100 mL of dry THF was cooled to −78° C. under argon and the former solution was added through a cannula to the latter solution over a period of 35 min. After 30 min, the cooling bath was removed and when the reaction had reached room temperature it was poured into 400 mL of water. The THF was evaporated and the remaining aqueous layer was extracted three times with diethyl ether. The combined ether phase was washed with water, dried (Na$_2$SO$_4$) and evaporated. Yield: 2.0 g (30%).

$^1$H NMR (500 MHz, CDCl$_3$) δ 7.4-7.25 (m, 2H), 5.01 (s, 1H, diasteromer), 4.91 (s, 1H, diasteromer), 2.88 (s, 3H, diasteromer), 2.52 (s, 3H, diasteromer), 2.49 (s, 3H, diasteromer), 2.34 (s, 3H, diasteromer), 1.72 (broad, 1H)

(ii) 2,6-Difluoro-4-formylbenzonitrile 2,6-Difluoro-4[(methylsulfinyl)(methylthio)methyl]benzonitrile (2.17 g, 8.32 mmol; see step (i) above) was dissolved in 90 mL of THF and 3.5 mL of concentrated sulfuric acid was added. The mixture was left at room temperature for 3 days and subsequently poured into 450 mL of water. Extraction three times with EtOAc followed and the combined ethereal phase was washed twice with aqueous sodium bicarbonate and with brine, dried (Na$_2$SO$_4$) and evaporated. Yield: 1.36 g (98%). The position of the formyl group was established by $^{13}$C NMR. The signal from the fluorinated carbons at 162.7 ppm exhibited the expected coupling pattern with two coupling constants in the order of 260 Hz and 6.3 Hz respectively corresponding to an ipso and a meta coupling from the fluorine atoms.

$^1$H NMR (400 MHz, CDCl$_3$) δ 10.35 (s, 1H), 7.33 (m, 2H)

(iii) 2.6-Difluoro-4-hydroxymethylbenzonitrile 2,6-Difluoro-4-formylbenzonitrile (1.36 g, 8.13 mmol; see step (ii) above) was dissolved in 25 mL of methanol and cooled on an ice bath. Sodium borohydride (0.307 g, 8.12 mmol) was added in portions with stirring and the reaction was left for 65 min. The solvent was evaporated and the residue was partitioned between diethyl ether and aqueous sodium bicarbonate. The ethereal layer was washed with more aqueous sodium bicarbonate and brine, dried (Na$_2$SO$_4$) and evaporated. The crude product crystallised soon and could be used without further purification. Yield: 1.24 g (90%).

$^1$H NMR (400 MHz, CDCl$_3$) δ 7.24 (m, 2H), 4.81 (s, 2H), 2.10 (broad, 1H)

(iv) 4-Cyano-2,6-difluorobenzyl methanesulfonate

To an ice cooled solution of 2,6-difluoro-4-hydroxymethylbenzonitrile (1.24 g, 7.32 mmol; see step (iii) above) and methanesulfonyl chloride (0.93 g, 8.1 mmol) in 60 mL of methylene chloride was added triethylamine (0.81 g, 8.1 mmol) with stirring. After 3 h at 0° C., the mixture was washed twice with 1M HCl and once with water, dried Na$_2$SO$_4$) and evaporated. The product could be used without further purification. Yield: 1.61 g (89%).

$^1$H NMR (300 MHz, CDCl$_3$) δ 7.29 (m, 2H), 5.33 (s, 2H), 3.07 (s, 3H)

(v) 4-Azidomethyl-2.6-difluorobenzonitrile

A mixture of 4-cyano-2,6-difluorobenzyl methanesulfonate (1.61 g, 6.51 mmol; see step (iv) above) and sodium azide (0.72 g, 0.0111 mol) in 10 mL of water and 20 mL of DMF was stirred at room temperature overnight. The resultant was subsequently poured into 200 mL of water and extracted three times with diethyl ether. The combined ethereal phase was washed five times with water, dried (Na$_2$SO$_4$) and evaporated. A small sample was evaporated for NMR purposes and the product crystallised. The rest was evaporated cautiously but not until complete dryness. Yield (theoretically 1.26 g) was assumed to be almost quantitative based on NMR and analytical HPLC.

$^1$H NMR (400 MHz, CDCl$_3$) δ 7.29 (m, 2H), 4.46 (s, 2H)

(vi) 4-Aminomethyl-2,6-difluorobenzonitrile

This reaction was carried out according to the procedure described in J. Chem. Res. (M) (1992) 3128. To a suspension of 520 mg of 10% Pd/C (50% moisture) in 20 mL of water was added a solution of sodium borohydride (0.834 g, 0.0221 mol) in 20 mL of water. Some gas evolution resulted. 4-Azidomethyl-2,6-difluorobenzonitrile (1.26 g, 6.49 mmol; see step (v) above) was dissolved in 50 mL of THF and added to the aqueous mixture on an ice bath over 15 min. The mixture was stirred for 4 h, whereafter 20 mL of 2M HCl was added and the mixture was filtered through Celite. The Celite was rinsed with more water and the combined aqueous phase was washed with EtOAc and subsequently made alkaline with 2M NaOH. Extraction three times with methylene chloride followed and the combined organic phase was washed with water, dried (Na$_2$SO$_4$) and evaporated. Yield: 0.87 g (80%).

$^1$H NMR (400 MHz, CDCl$_3$) δ 7.20 (m, 2H), 3.96 (s, 2H), 1.51 (broad, 2H)

(vii) 2,6-Difluoro-4-tert-butoxycarbonylaminomethylbenzonitrile

A solution of 4-aminomethyl-2,6-difluorobenzonitrile (0.876 g, 5.21 mmol; see step (vi) above) was dissolved in 50 mL of THF and di-tert-butyl dicarbonate (1.14 g, 5.22 mmol) in 10 mL of THF was added. The mixture was stirred for 3.5 h. The THF was evaporated and the residue was partitioned between water and EtOAc. The organic layer was washed three times with 0.5 M HCl and water, dried (Na$_2$SO$_4$) and evaporated. The product could be used without further purification. Yield: 1.38 g (99%).

$^1$H NMR (300 MHz, CDCl$_3$) δ 7.21 (m, 2H), 4.95 (broad, 1H), 4.43 (broad, 2H), 1.52 (s, 9H)

(viii) Boc-Pab(2,6-diF)(OH)

A mixture of 2,6-difluoro-4-tert-butoxycarbonylaminomethylbenzonitrile (1.38 g, 5.16 mmol; see step (vii) above), hydroxylamine hydrochloride (1.08 g, 0.0155 mol) and triethylamine (1.57 g, 0.0155 mol) in 20 mL of ethanol was stirred at room temperature for 36 h. The solvent was evaporated and the residue was partitioned between water and methylene chloride. The organic layer was washed with water, dried (Na$_2$SO$_4$) and evaporated. The product could be used without further purification. Yield: 1.43 g (92%).

$^1$H NMR (500 MHz, CD$_3$OD) δ 7.14 (m, 2H), 4.97 (broad, 1H), 4.84 (broad, 2H), 4.40 (broad, 2H), 1.43 (s, 9H)

(ix) Boc-Pab(2,6-diF)×HOAc

This reaction was carried out according to the procedure described by Judkins et al, Synth. Comm. (1998) 4351. Boc-Pab(2,6-diF)(OH) (1.32 g, 4.37 mmol; see step (viii) above), acetic anhydride (0.477 g, 4.68 mmol) and 442 mg of 10% Pd/C (50% moisture) in 100 mL of acetic acid was hydrogenated at 5 atm pressure for 3.5 h. The mixture was filtered through Celite, rinsed with ethanol and evaporated. The residue was freeze-dried from acetonitrile and water and a few drops of ethanol. The sub-title product could be used without further purification. Yield: 1.49 g (99%).

$^1$H NMR (400 MHz, CD$_3$OD) δ 7.45 (m, 2H), 4.34 (s, 2H), 1.90 (s, 3H), 1.40 (s, 9H)

(x) Boc-Pab(2,6-diF)(Teoc)

To a solution of Boc-Pab(2,6-diF)×HOAc (1.56 g, 5.49 mmol; see step (ix) above) in 100 mL of THF and 1 mL of water was added 2-(trimethylsilyl)ethyl p-nitrophenyl carbonate (1.67 g, 5.89 mmol). A solution of potassium carbonate (1.57 g, 0.0114 mol) in 20 mL of water was added dropwise over 5 min. The mixture was stirred overnight. The THF was evaporated and the residue was partitioned between water and methylene chloride. The aqueous layer was extracted with methylene chloride and the combined organic phase was washed twice with aqueous sodium bicarbonate, dried (Na$_2$SO$_4$) and evaporated. Flash chromatography on silica gel with heptane/EtOAc=2/1 gave 1.71 g (73%) of pure compound.

$^1$H NMR (400 MHz, CDCl$_3$) δ 7.43 (m, 2H), 4.97 (broad, 1H), 4.41 (broad, 2H), 4.24 (m, 2H), 1.41 (s, 9H), 1.11 (m, 2H), 0.06 (s, 9H)

(xi) Boc-Aze-Pab(2,6-diF)(Teoc)

Boc-Pab(2,6-diF)(Teoc) (1.009 g; 2.35 mmol; see step (x) above) was dissolved in 50 mL of EtOAc saturated with HCl(g). The mixture was left for 10 min., evaporated and dissolved in 18 mL of DMF, and then cooled on an ice bath. Boc-Aze-OH (0.450 g, 2.24 mmol), PyBOP (1.24 g, 2.35 mmol) and lastly diisopropylethyl amine (1.158 g, 8.96 mmol) were added. The reaction mixture was stirred for 2 h and then poured into 350 mL of water and extracted three times with EtOAc. The combined organic phase was washed with brine, dried (Na$_2$SO$_4$) and evaporated. Flash chromatography on silica gel with heptane:EtOAc (1:3) gave 1.097 g (96%) of the desired compound.

$^1$H NMR (500 MHz, CDCl$_3$) δ 7.46 (m, 2H), 4.65-4.5 (m, 3), 4.23 (m, 2H), 3.87 (m, 1H), 3.74 (m, 1H), 2.45-2.3 (m, 2H), 1.40 (s, 9H), 1.10 (m, 2H), 0.05 (s, 9H)

(xii) Ph(3-Cl)(5-OCHF$_2$)—(R)CH(OH)C(O)-Aze-Pab(2,6-diF)(Teoc)

Boc-Aze-Pab(2,6-diF)(Teoc) (0.256 g, 0.500 mmol; see step (xi) above) was dissolved in 20 mL of EtOAc saturated with HCl(g). The mixture was left for 10 min. and evaporated and dissolved in 5 mL of DMF. Ph(3-Cl)(5-OCHF$_2$)—(R)CH(OH)C(O)OH (0.120 g, 0.475 mmol; see Preparation A(viii) above), PyBOP (0.263 g, 0.498 mmol) and lastly diisopropylethyl amine (0.245 g, 1.89 mmol) were added. The reaction mixture was stirred for 2 h and then poured into 350 mL of water and extracted three times with EtOAc. The combined organic phase was washed with brine, dried (Na$_2$SO$_4$) and evaporated. Flash chromatography on silica gel with EtOAc gave 0.184 g (60%) of the desired sub-title compound.

$^1$H NMR (400 MHz, CD$_3$OD, mixture of rotamers) δ 7.55-7.45 (m, 2H), 7.32 (m, 1H, major rotamer), 7.27 (m, 1H, minor rotamer), 7.2-7.1 (m, 2H), 6.90 (t, 1H, major rotamer), 6.86 (t, 1H, minor rotamer), 5.15 (s, 1H, major rotamer), 5.12 (m, 1H, minor rotamer), 5.06 (s, 1H, minor rotamer), 4.72 (m, 1H, major rotamer), 4.6-4.45 (m, 2H), 4.30 (m, 1H, major rotamer), 4.24 (m, 2H), 4.13 (m, 1H, minor rotamer), 4.04 (m, 1H, minor rotamer), 3.95 (m, 1H, minor rotamer), 2.62 (m, 1H, minor rotamer), 2.48 (m, 1H, major rotamer), 2.22 (m, 1H, major rotamer), 2.10 (m, 1H, minor rotamer), 1.07 (m, 2H), 0.07 (m, 9H)

(xiii) Ph(3-Cl)(5-OCHF)—(R)CH(OH)C(O)-Aze-Pab(2,6-diF)(OMe, Teoc)

A mixture of Ph(3-Cl)(5-OCHF$_2$)—(R)CH(OH)C(O)-Aze-Pab(2,6-diF)(Teoc) (64 mg, 0.099 mmol; see step (xii) above) and O-methyl hydroxylamine hydrochloride (50 mg, 0.60 mmol) in 4 mL of acetonitrile was heated at 70° C. for 3 h. The solvent was evaporated and the residue was partitioned between water and EtOAc. The aqueous layer was extracted twice with EtOAc and the combined organic phase was washed with water, dried (Na$_2$SO$_4$) and evaporated. The product could be used without further purification. Yield: 58 mg (87%).

$^1$H NMR (400 MHz, CDCl$_3$) δ 7.90 (bt, 1H), 7.46 (m, 1H), 7.25-6.95 (m, 5H), 6.51, t, 1H), 4.88 (s, 1H), 4.83 (m, 1H), 4.6-4.5 (m, 2H), 4.4-3.9 (m, 4H), 3.95 (s, 3H), 3.63 (m, 1H), 2.67 (m, 1H), 2.38 (m, 1H), 1.87 (broad, 1H), 0.98 (m, 2H), 0.01, s, 9H)

(xiv) Ph(3-Cl)(5-OCHF$_2$)—(R)CH(OH)C(O)—(S)Aze-Pab(2,6-diF)(OMe)

Ph(3-Cl)(5-OCHF$_2$)—(R)CH(OH)C(O)-Aze-Pab(2,6-diF)(OMe,Teoc) (58 mg, 0.086 mmol; see step (xiii) above) was dissolved in 3 mL of TFA, cooled on an ice bath and allowed to react for 2 h. The TFA was evaporated and the residue dissolved in EtOAc. The organic layer was washed twice with aqueous sodium carbonate and water, dried (Na$_2$SO$_4$) and evaporated. The residue was freeze-dried from water and acetonitrile to give 42 mg (92%) of the title compound.

$^1$H NMR (300 MHz, CDCl$_3$) δ 7.95 (bt, 1H), 7.2-7.1 (m, 4H), 6.99 (m, 1H), 6.52 (t, 1H), 4.88 (s, 1H), 4.85-4.75 (m, 3H), 4.6-4.45 (m, 2H), 4.29 (broad, 1H), 4.09 (m, 1H), 3.89 (s, 3H), 3.69 (m, 1H), 2.64 (m, 1H), 2.38 (m, 1H), 1.85 (broad, 1H) $^{13}$C-NMR (100 MHz; CDCl$_3$): (carbonyl and/or amidine carbons) δ 172.1, 169.8, 151.9 APCI-MS: (M+1)=533/535 m/z Preparation of Compound E (Ph(3-Cl)(5-OCH$_2$CH$_2$F)—(R)CH(OH)C(O)—(S)Aze-Pab(OMe))

(i) (2-Monofluoroethyl) methanesulfonate

To a magnetically stirred solution of 2-fluoroethanol (5.0 g, 78.0 mmol) in CH$_2$Cl$_2$ (90 mL) under nitrogen at 0° C. was added triethylamine (23.7 g, 234 mmol) and methanesulfonyl chloride (10.7 g, 93.7 mmol). The mixture was stirred at 0° C. for 1.5 h, diluted with CH$_2$Cl$_2$ (100 mL) and washed with 2N HCl (100 mL). The aqueous layer was extracted with CH$_2$Cl$_2$ (50 mL) and the combined organic extracts washed with brine (75 mL), dried (Na$_2$SO$_4$), filtered and concentrated in vacuo to afford the sub-title compound (9.7 g, 88%) as a yellow oil which was used without further purification.

$^1$H NMR (300 MHz, CDCl$_3$) δ 4.76 (t, J=4 Hz, 1H), 4.64 (t, J=4 Hz, 1H), 4.52 (t, J=4 Hz, 1H), 4.43 (t, J=4 Hz, 1H), 3.09 (s, 3H).

(ii) 3-Chloro-5-monofluoroethoxybenzaldehyde

To a solution of 3-chloro-5-hydroxybenzaldehyde (8.2 g, 52.5 mmol; see Preparation A(ii) above) and potassium carbonate (9.4 g, 68.2 mmol) in DMF (10 mL) under nitrogen was added a solution of (2-monofluoroethyl) methanesulfonate (9.7 g, 68.2 mmol; see step (i) above) in DMF (120 mL) dropwise at room temperature. The mixture was heated to 100° C. for 5 h and then stirred overnight at room temperature. The reaction was cooled to 0° C., poured into ice-cold 2N HCl and extracted with EtOAc. The combined organic extracts were washed with brine, dried (Na$_2$SO$_4$), filtered and concentrated in vacuo. The brown oil was chromatographed on silica gel eluting with Hex:EtOAc (4:1) to afford the sub-title compound (7.6 g, 71%) as a yellow oil.

$^1$H NMR (300 MHz, CDCl$_3$) δ 9.92 (s, 1H), 7.48 (s, 1H), 7.32 (s, 1H), 7.21 (s, 1H), 4.87 (t, J=4 Hz, 1H), 4.71 (t, J=3 Hz, 1H), 4.33 (t, J=3 Hz, 1H), 4.24 (t, J=3 Hz, 1H).

(iii) Ph(3-Cl)(5-OCH$_2$CH$_2$F)—(R,S)CH(OTMS)CN

To a solution of 3-chloro-5-monofluoroethoxybenzaldehyde (7.6 g, 37.5 mmol; see step (ii) above) and zinc iodide (3.0 g, 9.38 mmol) in CH$_2$Cl$_2$ (310 mL) was added trimethylsilyl cyanide (7.4 g, 75.0 mmol) dropwise at 0° C. under nitrogen. The mixture was stirred at 0° C. for 3 h and at room temperature overnight. The reaction was diluted with H$_2$O (300 mL), the organic layer was separated, dried (Na$_2$SO$_4$), filtered and concentrated in vacuo to afford the sub-title compound (10.6 g, 94%) as a brown oil that was used without further purification or characterisation.

(iv) Ph(3-Cl)(5-OCH$_2$CH$_2$F)—(R,S)CH(OH)C(O)OH

Concentrated hydrochloric acid (100 mL) was added to Ph(3-Cl)(5-OCH$_2$CH$_2$F)—(R,S)CH(OTMS)CN (10.6 g, 5.8 mmol; see step (iii) above) and the solution stirred at 100° C. for 3 h. After cooling to room temperature, the reaction was further cooled to 0° C., basified slowly with 3N NaOH (~300 mL) and washed with Et$_2$O (3×200 mL). The aqueous layer was acidified with 2N HCl (80 mL) and extracted with EtOAc (3×300 mL). The combined EtOAc extracts were dried (Na$_2$SO$_4$), filtered and concentrated in vacuo to afford the sub-title compound (8.6 g, 98%) as a pale yellow solid that was used without further purification.

R$_f$=0.28 (90:8:2 CHCl$_3$:MeOH:concentrated NH$_4$OH)

$^1$H NMR (300 MHz, CD$_3$OD) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1).

(v) Ph(3-Cl)(5-OCH$_2$CH$_2$F)—(S)CH(OAc)C(O)OH (a) and Ph(3-Cl)(5-OCH$_2$CH$_2$F)—(R)CH(OH)C(O)OH (b)

A solution of Ph(3-Cl)(5-OCH$_2$CH$_2$F)—(R,S)CH(OH)C(O)OH (8.6 g, 34.5 mmol; see step (iv) above) and Lipase PS "Amano" (4.0 g) in vinyl acetate (250 mL) and MTBE (250 mL) was heated at 70° C. under nitrogen for 3 d. The reaction was cooled to room temperature and the enzyme removed by filtration through Celite®. The filter cake was washed with EtOAc and the filtrate concentrated in vacuo. Chromatography on silica gel eluting with CHCl$_3$:MeOH:Et$_3$N (90:8:2) afforded the triethylamine salt of sub-title compound (a) as a yellow oil. In addition, the triethylamine salt of sub-title compound (b) (4.0 g) was obtained. The salt of sub-title compound (b) was dissolved in H$_2$O (250 mL), acidified with 2N HCl and extracted with EtOAc (3×200 mL). The combined organic extracts were dried (Na$_2$SO$_4$), filtered and concentrated in vacuo to yield the sub-title compound (b) (2.8 g, 32%) as a yellow oil.

Data for Sub-Title Compound (b):

R$_f$=0.28 (90:8:2 CHCl$_3$:MeOH:concentrated NH$_4$OH)

$^1$H NMR (300 MHz, CD$_3$OD) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1H).

(vi) Ph(3-Cl)(5-OCH$_2$CH$_2$F)—(R)CH(OH)C(O)—(S)Aze-Pab(OMe)

To a solution of Ph(3-Cl)(5-OCH$_2$CH$_2$F)—(R)CH(OH)C(O)OH (818 mg, 3.29 mmol; see step (v) above) in DMF (30 mL) under nitrogen at 0° C. was added HAze-Pab(OMe).2HCl (1.43 g, 4.27 mmol, see international patent application WO 00/42059), PyBOP (1.89 g, 3.68 mmol), and DIPEA (1.06 g, 8.23 mmol). The reaction was stirred at 020 C. for 2 h and then at room temperature overnight. The mixture was concentrated in vacuo and the residue chromatographed two times on silica gel, eluting first with CHCl$_3$:EtOH (15:1) and second with EtOAc:EtOH (20:1) to afford the title compound (880 mg, 54%).

R$_f$=0.60 (10:1 CHCl$_3$:EtOH)

$^1$H NMR (300 MHz, CD$_3$OD, complex mixture of rotamers) δ 7.58-7.60 (d, J=8 Hz, 2H), 7.34 (d, J=7 Hz, 2H), 7.05-7.08 (m, 2H), 6.95-6.99 (m, 1H), 5.08-5.13 (m, 1H), 4.77-4.82 (m, 1M), 4.60-4.68 (m, 1H), 3.99-4.51 (m, 7H), 3.82 (s, 3H), 2.10-2.75 (m, 2H).

$^{13}$C-NMR (150 MHz; CD$_3$OD): (carbonyl and/or amidine carbons) δ 173.3, 170.8, 152.5.

APCI-MS: (M+1)=493 m/z.

Preparation of Compound F (Ph(3-Cl)(5-OCHF$_2$)—(R)CH(OH)C(O)-Aze-Pab(OH))

(i) Ph(3-Cl)(5-OCHF$_2$)—(R)CH(OH)C(O)-Aze-Pab(OH.Teoc)

Ph(3-Cl)(5-OCHF$_2$)—(R)CH(OH)C(O)-Aze-Pab(Teoc) (0.148 g, 0.24 mmol; see Preparation D step (ix) above), was dissolved in 9 mL of acetonitrile and 0.101 g (1.45 mmol) of hydroxylamine hydrochloride was added. The mixture was heated at 70° C. for 2.5 h, filtered through Celite® and evaporated. The crude product (0.145 g; 75% pure) was used directly in the next step without further purification.

(ii) Ph(3-Cl)(5-OCHF)—(R)CH(OH)C(O)-Aze-Pab(OH)

Ph(3-Cl)(5-OCHF$_2$)—(R)CH(OH)C(O)-Aze-Pab(OH, Teoc) (0.145 g, 0.23 mmol; see step (i) above), was dissolved in 0.5 mL of CH$_2$Cl$_2$ and 9 mL of TFA. The reaction was allowed to proceed for 60 minutes. TFA was evaporated and the residue was purified using preparative HPLC. The fractions of interest were pooled and freeze-dried (2×), yielding 72 mg (yield over two steps 62%) of the title compound.

MS (m/z) 482 (M−1)$^-$; 484 (M+1)$^+$ $^1$H-NMR (400 MHz; CD$_3$OD): δ 7.58 (d, 2H), 7.33 (m, 3H), 7.15 (m, 2H), 6.89 (t, 1H major rotamer), 6.86 (t, 1H minor rotamer), 5.18 (s, 1H major rotamer; and m, 1H minor rotamer), 5.12 (s, 1H minor rotamer), 4.77 (m, 1H major rotamer), 4.42 (m, 2H), 4.34 (m, 1H major rotamer), 4.14 (m, 1H major rotamer), 4.06 (m, 1H minor rotamer), 3.95 (m, 1H minor rotamer), 2.66 (m, 1H minor rotamer), 2.50 (m, 1H major rotamer), 2.27 (m, 1H major rotamer), 2.14 (m, 1H minor rotamer)

$^{13}$C-NMR (100 MHz; CD$_3$OD): (carbonyl and/or amidine carbons, rotamers) δ 172.4, 172.3, 172.0, 171.4 152.3, 152.1

Preparation of Compound H (Ph(3-Cl)(5-OCH$_2$CHF)—(R)CH(OH)C(O)-Aze-Pab(OH))

(i) Ph(3-Cl)(5-OCH$_2$CHF$_2$)—(R)CH(OH)C(O)-Aze-Pab(Z)

Boc-Aze-Pab(Z) (see international patent application WO 97/02284, 92 mg, 0.197 mmol) was dissolved in 10 mL of EtOAc saturated with HCl(g) and allowed to react for 10 min. The solvent was evaporated and the residue was mixed with Ph(3-Cl)(5-OCH$_2$CHF$_2$)—(R)CH(OH)C(O)OH (50 mg, 0.188 mmol), PyBOP (109 mg, 0.209 mmol) and finally diisopropylethyl amine (96 mg, 0.75 mmol) in 2 mL of DMF. The mixture was stirred for 2 h and then poured into 50 mL of water and extracted three times with EtOAc. The combined organic phase was washed with water, dried (Na$_2$SO$_4$) and evaporated. The crude product was flash chromatographed on silica gel with EtOAc:MeOH (9:1). Yield: 100 mg (87%).

$^1$H NMR (300 MHz, CD$_3$OD mixture of rotamers) δ 7.85-7.75 (m, 2H), 7.45-7.25 (m, 7H), 7.11 (m, 1H, major rotamer), 7.08 (m, 1H, minor rotamer), 7.05-6.9 (m, 2H), 6.13 (bt, 1H), 5.25-5.05 (m, 3H), 4.77 (m, 1H, partially hidden by the CD$_3$OH signal), 4.5-3.9 (m, 7H), 2.64 (m, 1H, minor rotamer), 2.47 (m, 1H, major rotamer), 2.25 (m, 1H, major rotamer), 2.13 (m, 1H, minor rotamer)

(ii) Ph(3-Cl)(5-OCH—CHF$_2$)—(R)CH(OH)C(O)-Aze-Pab(OH)

Hydroxylamine hydrochloride (65 mg, 0.94 mmol) and triethylamine (0.319 g, 3.16 mmol) were mixed in 8 mL of THF and sonicated for 1 h at 40° C. Ph(3-Ca)(5-OCH$_2$CHF$_2$)—(R)CH(OH)C(O)-Aze-Pab(Z) (96 mg, 0.156 mmol; see step (i) above) was added with 8 mL more of THF. The mixture was stirred at 40° C. for 4.5 days. The solvent was evaporated and the crude product was purified by preparative RPLC with CH$_3$CN:0.1M NH$_4$OAc (40:60). Yield: 30 mg (38%). Purity: 99%.

¹H NMR (300 MHz, CD₃OD mixture of rotamers) δ 7.6-7.55 (m, 2H), 7.35-7.3 (m, 2H), 7.12 (m, 1H, major rotamer), 7.09 (m, 1H, minor rotamer), 7.05-6.9 (m, 2H), 6.15 (triplet of multiplets, 1H), 5.15 (m, 1H, minor rotamer), 5.13 (s, 1H, major rotamer), 5.08 (s, 1H, minor rotamer), 4.77 (m, 1H, major rotamer), 4.5-4.2 (m, 5H), 4.08 (m, 1H, major rotamer), 3.97 (m, 1H, minor rotamer), 2.66 (m, 1H, minor rotamer), 2.50 (m, 1H major rotamer), 2.27 (m, 1H, major rotamer), 2.14 (m, 1H, minor rotamer).

¹³C-NMR (100 MHz; CD₃OD): (carbonyl and/or amidine carbons, mixture of rotamers) δ 172.8, 172.2, 171.4, 159.1, 158.9, 154.2.

APCI-MS: (M+1)=497/499 m/z

Abbreviations
Ac=acetyl
APCI=atmospheric pressure chemical ionisation (in relation to MS)
API=atmospheric pressure ionisation (in relation to MS)
aq.=aqueous
Aze(&(S)-Aze)=(S)-azetidine-2-carboxylate (unless otherwise specified)
Boc=tert-butyloxycarbonyl
br=broad (in relation to NMR)
CI=chemical ionisation (in relation to MS)
d=day(s)
d=doublet (in relation to NMR)
DCC=dicyclohexyl carbodiimide
dd=doublet of doublets (in relation to NMR)
DIBAL-H=di-isobutylaluminium hydride
DIPEA=diisopropylethylamine
DMAP=4-(N,N-dimethyl amino) pyridine
DMF=N,N -dimethylformamide
DMSO=dimethylsulfoxide
DSC=differential scanning colorimetry
DVT=deep vein thrombosis
EDC=1-(3-dimethylaminopropyl)-3-ethylcarbodiimide hydrochloride
eq.=equivalents
ES=electrospray
ESI=electrospray interface
Et=ethyl
ether=diethyl ether
EtOAc=ethyl acetate
EtOH=ethanol
Et₂O=diethyl ether
HATU=O-(azabenzotriazol-1-yl)-N,N,N',N'-tetramethyluronium hexafluorophosphate
HBTU=[N,N,N',N'-tetramethyl-O-(benzotriazol-1-yl)uronium hexafluorophosphate]
HCl=hydrochloric acid, hydrogen chloride gas or hydrochloride salt (depending on context)
Hex=hexanes
HOAc=acetic acid
HPLC=high performance liquid chromatography
LC=liquid chromatography
m=multiplet (in relation to NMR)
Me=methyl
MeOH=methanol
min.=minute(s)
MS=mass spectroscopy
MTBE=methyl tert-butyl ether
NMR=nuclear magnetic resonance
OAc=acetate
Pab=para-amidinobenzylamino
H-Pab=para-amidinobenzylamine
Pd/C=palladium on carbon
Ph=phenyl
PyBOP=(benzotriazol-1-yloxy)tripyrrolidinophosphonium hexafluorophosphate
q=quartet (in relation to NMR)
QF=tetrabutylammonium fluoride
rt/RT=room temperature
s=singlet (in relation to NMR)
t=triplet (in relation to NMR)
TBTU=[N,N,N',N'-tetramethyl-O-(benzotriazol-1-yl)uronium tetrafluoroborate]
TEA=triethylamine
Teoc=2-(trimethylsilyl)ethoxycarbonyl
TEMPO=2,2,6,6-tetramethyl-1-piperidinyloxy free radical
TFA=trifluoroacetic acid
TGA=thermogravimetric analysis
THF=tetrahydrofuran
TLC=thin layer chromatography
UV=ultraviolet Prefixes n-, s-, i-, t- and tert- have their usual meanings: normal, secondary, iso, and tertiary.

Examples 1-5 and 8-14 illustrate the invention. Examples 6 and 7 are present for comparative purposes only and do not form part of the present invention. In the Examples and Figures the ratios given in brackets refer to the weight % ratio of neutral gelling polymer to iota-Carrageenan and do not take into account the basic pharmaceutically active ingredient or any other component that might be present. In the accompanying Figures:

FIG. 1: Release of H376/95 from blends with varying composition ratio of iota-Carrageenan and PEO, 4 M. Tablets were analysed for 2 hours at pH 1 and for the remaining time at pH 6.8.

Figure 2:
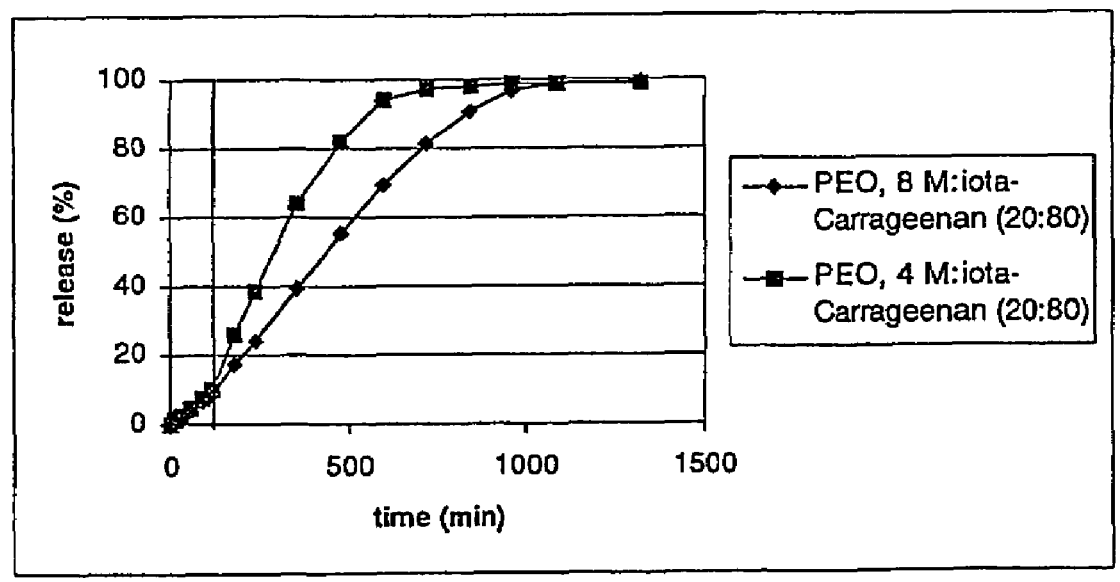

FIG. 2: Release of H376/95 from blends with composition ratio (20:80) of PEO with different molecular weight and iota-Carrageenan. Tablets were analysed for 2 hours at pH 1 and for the remaining time at pH 6.8.

Figure 3:
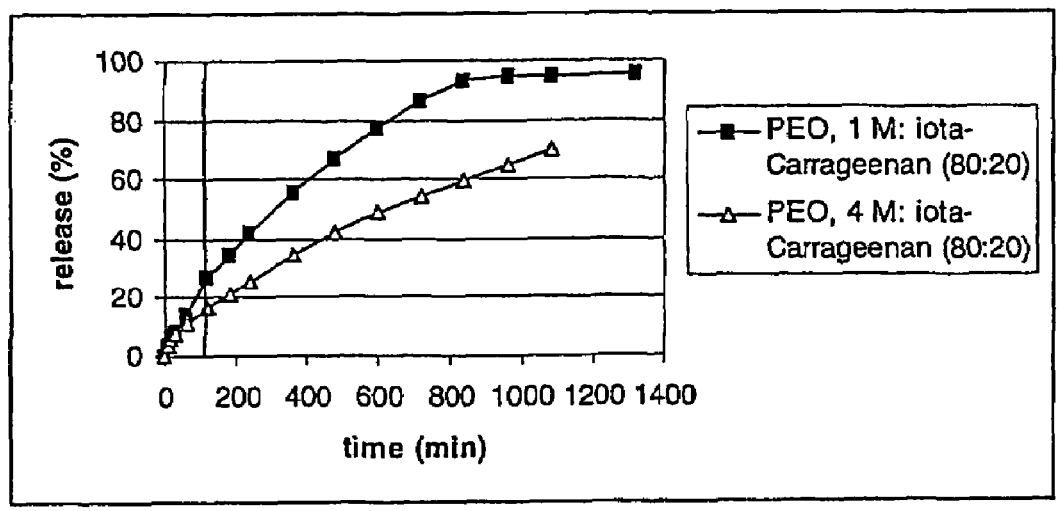

FIG. 3: Release of H376/95 from blends with composition ratio (80:20) of PEO with different molecular weight and iota-Carrageenan. Tablets were analysed for 2 hours at pH 1 and for the remaining time at pH 6.8.

Figure 4:
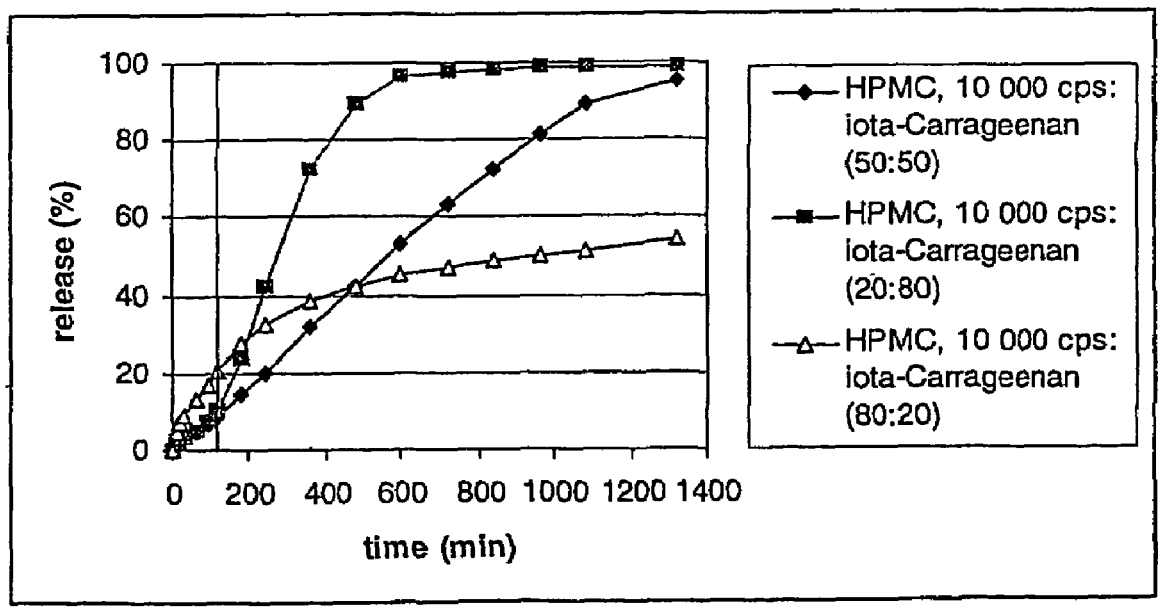

FIG. 4: Release of H376/95 from blends with varying composition ratio of iota-Carrageenan and HPMC, 10 000 cps. Tablets were analysed for 2 hours at pH 1 and for the remaining time at pH 6.8.

Figure 5:
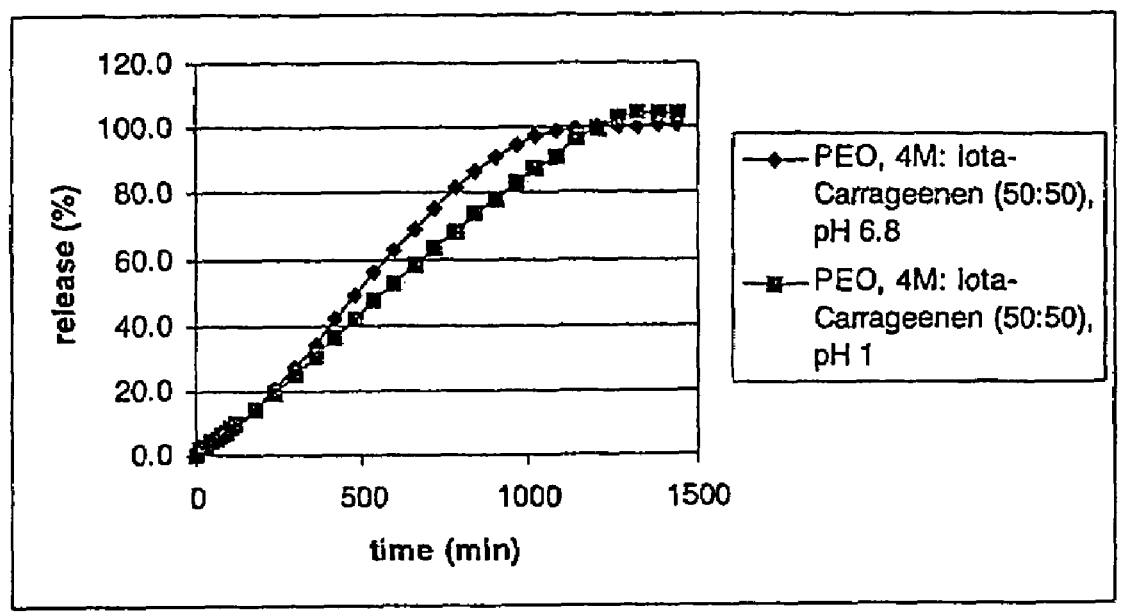

FIG. 5: Release of H376/95 from blends with the composition ratio (50:50) of PEO, 4 M and iota-Carrageenan. Tablets were analysed for 24 hours in different artificial media.

Figure 6:
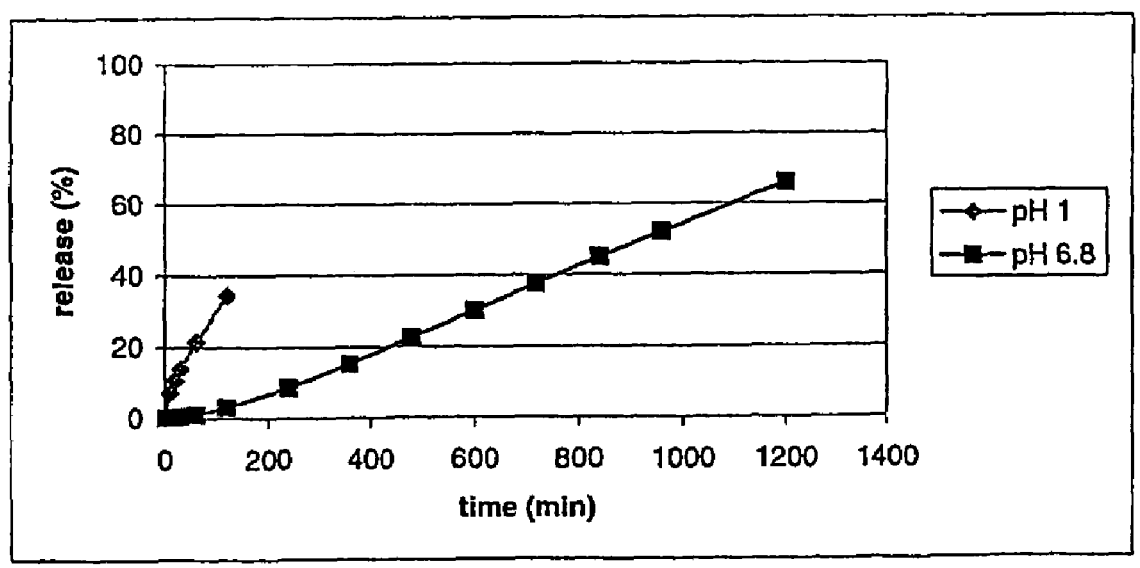

FIG. 6: Release of H376/95 from the neutral gelling polymer PEO 4 M, analysed in different artificial media.

Figure 7:
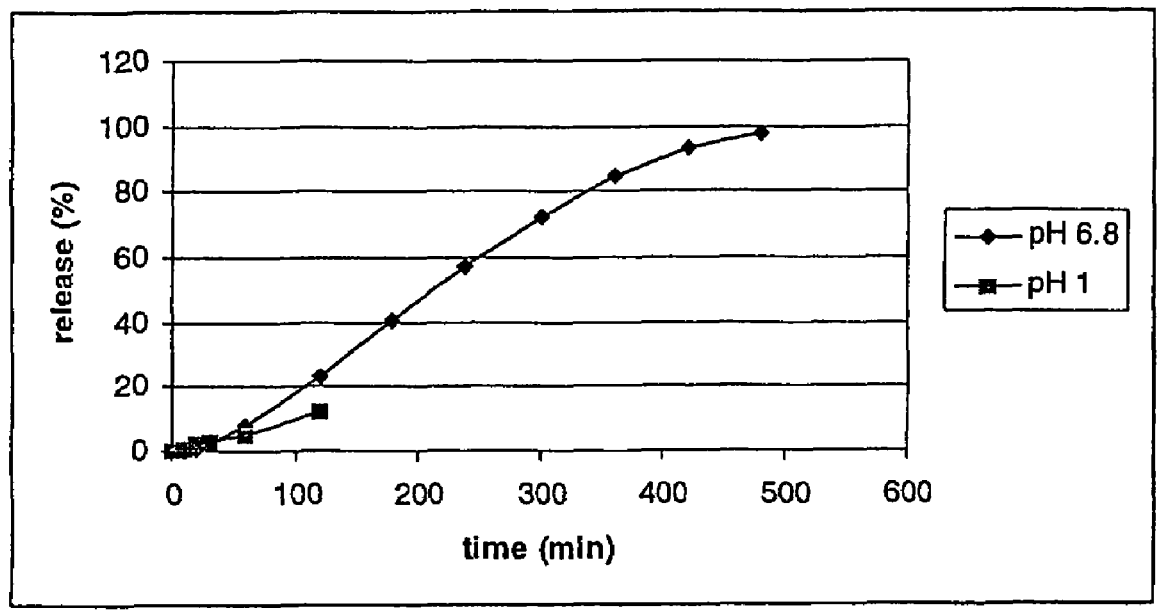

FIG. 7: Release of H376/95 from the anionic polymer iota-Carrageenan, analysed in different artificial media.

Figure 8:
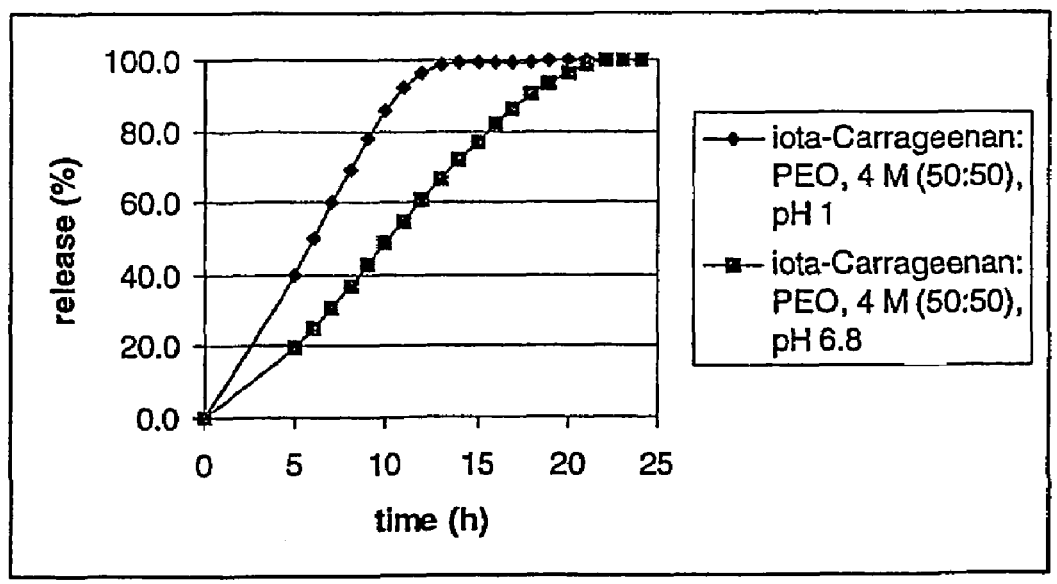

FIG. 8: Release of Compound A from blends with the composition ratio (50:50) of iota-Carrageenan and PEO, 4 M at pH 1 and 6.8. Tablets were analysed for 24 hours in different artificial media.

Figure 9:
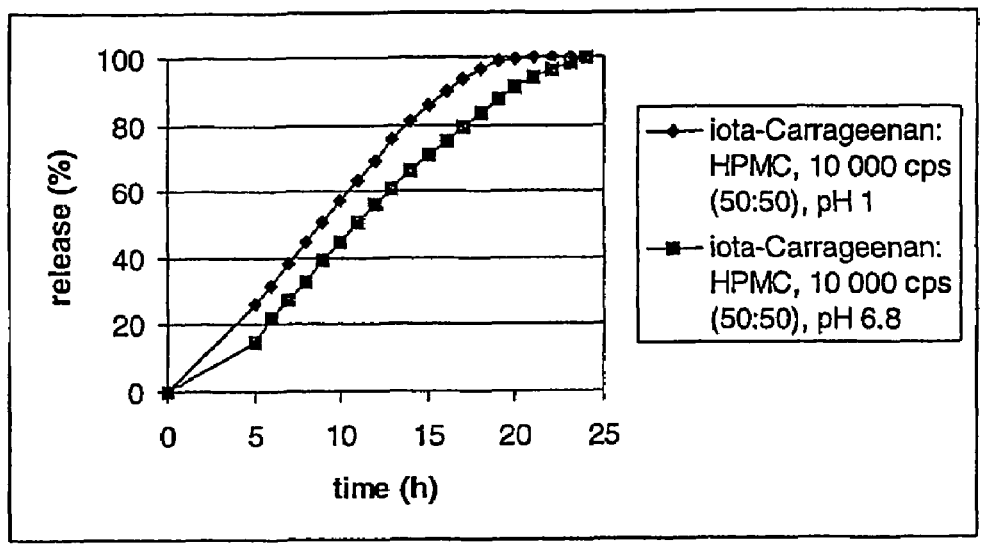

FIG. 9: Release of Compound A from blends with the composition ratio (50:50) of iota-Carrageenan and HPMC, 10,000 cps, at pH 1 and pH 6.8. Tablets were analysed for 24 hours in different artificial media.

Figure 10:
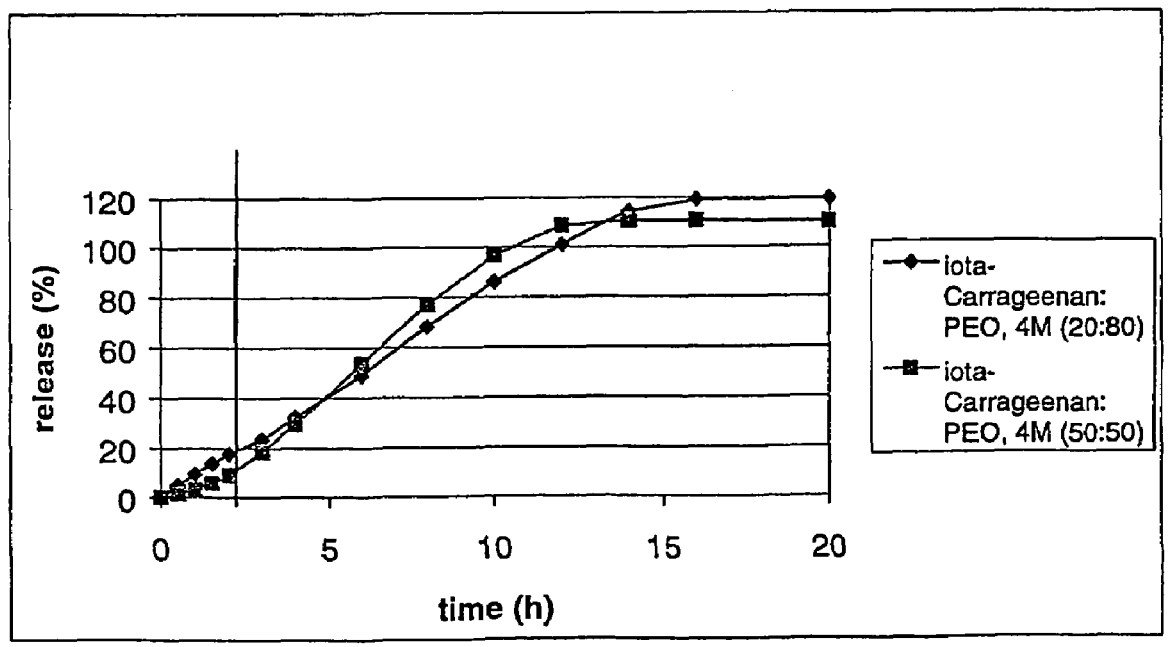

FIG. 10: Release of Compound B from iota-Carrageenan blended with the neutral polymer PEO, 4 M in the ratio (50:50) and (80:20). Tablets analysed for 2 hours in pH 1 and remaining time in pH 6.8.

Figure 11:
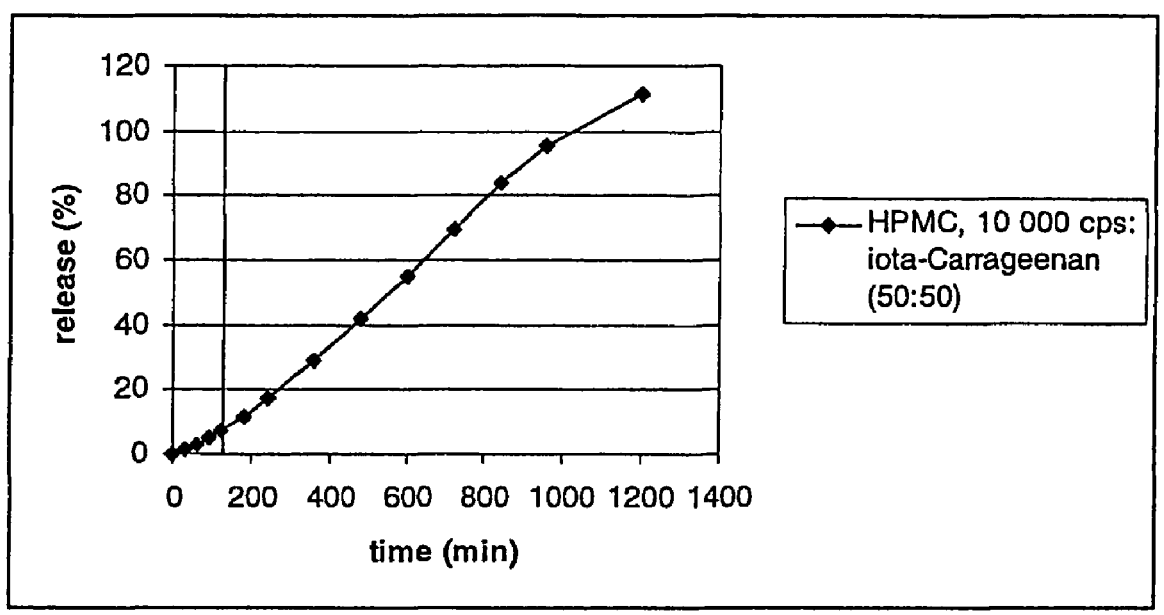

FIG. 11: Release of Compound B from iota-Carrageenan blended with the neutral polymer HPMC, 10 000 cps in the ratio (50:50). Tablets analysed for 2 hours in pH 1 and remaining time in pH 6.8.

EXAMPLE 1

This Example shows the release of H376/95 from blends with varying composition ratio of PEO, 4 M and iota-Carrageenan. Tablets were analysed for 2 hours at pH 1 and for the remaining time at pH 6.8.

| | Ratio PEO 4 M: iota-Carrageenan | | |
|---|---|---|---|
| | (80:20) | (50:50) | (20:80) |
| H376/95 | 50.5 mg | 50.5 mg | 50.5 mg |
| Polyethylene oxide, 4 M | 160.0 mg | 100.0 mg | 40.0 mg |
| Iota-Carrageenan | 40.0 mg | 100.0 mg | 160.0 mg |
| Sodium stearyl fumarate | 2.5 mg | 2.5 mg | 2.5 mg |
| Tablet weight | 253 mg | 253 mg | 253 mg |

Tablets were manufactured by direct compression. The active ingredient, PEO 4M and iota-Carrageenan were mixed thoroughly and a lubricant, sodium stearyl fumarate, was added though a 0.7-mm sieve. Additional final mixing was done and the mixture was compressed with a 9 mm punch in a single-punch tablet press. The tablets were analysed in a dissolution bath, UPS II (50 rpm, 37° C., artificial media) containing 0.1 M HCl, pH 1, for two hours. Thereafter the tablets were moved to a dissolution bath with a 0.1 M phosphate buffer, pH 6.8, and were further analysed. The results from the analysis are presented in FIG. 1. The (50:50) formulation shows an essentially pH-independent release profile at a pH range between 1-6.8. It can additionally be concluded that when blending different ratios of the anionic polymer, iota-Carrageenan, and the neutral gelling polymer PEO 4 M, the release rate in media with different pH can be modified.

EXAMPLE 2

This Example shows the release of H376/95 from blends with composition ratio (20:80) of PEO with different molecular weight and iota-Carrageenan. Tablets were analysed for 2 hours at pH 1 and for the remaining time at pH 6.8.

| Ratio PEO 4 M or 8 M: iota-Carrageenan(20:80) | |
|---|---|
| H376/95 | 50.5 mg |
| Polyethylene oxide | 40.0 mg |
| Iota-Carrageenan | 160.0 mg |
| Sodium stearyl fumarate | 2.5 mg |
| Tablet weight | 253 mg |

Tablets were manufactured and analysed according to Example 1. The results from the analysis are presented in FIG. 2 and show that using higher molecular weight of the neutral gelling polymer gives a slower release rate in neutral pH. The release rate in the low pH region is not affected because there is a sufficient amount of anionic polymer included in the formulation.

EXAMPLE 3

This Example shows the release of H376/95 from blends with composition ratio (80:20) of PEO with different molecular weight to iota-Carrageenan. Tablets were analysed for 2 hours at pH 1 and the remaining time at pH 6.8.

| Ratio PEO 1 M or 4 M: iota-Carrageenan(80:20) | |
|---|---|
| H376/95 | 50.5 mg |
| Polyethylene oxide | 160.0 mg |
| Iota-Carrageenan | 40.0 mg |
| Sodium stearyl fumarate | 2.5 mg |
| Tablet weight | 253 mg |

Tablets were prepared and analysed according to Example 1. FIG. 3 shows how using a gelling polymer with higher molecular weight can decrease the release rate in neutral pH. At the same time the release-retarding effect in pH 1 is less distinct because a smaller amount of iota-Carrageenan is used, compared with the examples shown in FIG. 2.

EXAMPLE 4

This Example shows the release of H376/95 from blends with varying composition ratio of iota-Carrageenan and HPMC, 10 000 cps. Tablets were analysed for 2 hours at pH 1 and for the remaining time at pH 6.8.

| | Ratio HPMC: iota-Carrageenan | | |
|---|---|---|---|
| | (80:20) | (50:50) | (20:80) |
| H376/95 | 50.5 mg | 50.5 mg | 50.5 mg |
| HPMC, 10 000 cps | 160.0 mg | 100.0 mg | 40.0 mg |
| Iota-Carrageenan | 40.0 mg | 100.0 mg | 160.0 mg |
| Sodium stearyl fumarate | 2.5 mg | 2.5 mg | 2.5 mg |
| Tablet weight | 253 mg | 253 mg | 253 mg |

Tablets were manufactured and analysed according to Example 1. The results from the analysis in different dissolution media are presented in FIG. 4. The (50:50) formulation again shows an essentially pH-independent release profile at a pH range between 1-6.8. It can be concluded that the release rate again can be modified by blending different ratios of various other neutral gelling polymers, in this case HPMC, 10 000 cps, with the anionic polymer, iota-Carrageenan.

EXAMPLE 5

This Example shows the release of H376/95 from a blend with the composition ratio (50:50) of PEO 4M and iota-Carrageenan. Tablets were analysed for 24 hours in different media.

| Ratio PEO, 4 M: iota-Carrageenan(50:50) | |
|---|---|
| H376/95 | 50.5 mg |
| Polyethylene oxide, 4 M | 100.0 mg |
| Iota-Carrageenan | 100.0 mg |
| Sodium stearyl fumarate | 2.5 mg |
| Tablet weight | 253 mg |

Tablets were manufactured through direct compression, according to Example 1. The analyses were made in dissolution baths (USP apparatus 2 with tablets positioned in a basket[1] along the flow steam) where three tablets were analysed for 24 hours in each media, 0.1 M HCl and a 0.1 M phosphate buffer, pH 6.8 with 5% ethanol (EtOH), added to improve solubility of the drug. The results, presented in FIG. 5, clearly show that a tablet with a pH independent release profile can be made, when using a composition with equal parts of PEO, 4M and iota-Carrageenan.

[1 A custom made quadrangular basket of mesh wire, soldered in one of its upper, narrow sides to the end of a steel rod. The rod is brought through the cover of the dissolution vessel and fixed by means of two Teflon nuts, 3.2 cm from the centre of the vessel. The lower edge of the bottom of the basket is adjusted to be 1 cm above the paddle. The basket is directed along the flow stream with the tablet under test standing on its edge.]

EXAMPLE 6

This Example shows the release of H376/95 from the neutral gelling polymer PEO 4M in the absence of iota-carrageenan and analysed in different artificial media.

| | |
|---|---|
| H376/95 | 50.5 mg |
| Polyethylene oxide, 4 M | 200.0 mg |
| Sodium stearyl fumarate | 2.5 mg |
| Tablet weight | 253 mg |

Tablets were manufactured through direct compression, according to Example 1. Analyses were performed separately in different dissolution baths. The tablets in the vessels containing 0.1 M HCl were analysed for 2 hours. When using 0.1 M phosphate buffer pH 6.8 as the dissolution media, the tablets were analysed for 20 hours. The results in FIG. 6 show that the release rate in pH 1 is significantly greater than the release in pH 6.8, indicating that using the neutral polymer alone is not sufficient to give a pH independent release profile for a basic drug possessing a pH dependent solubility.

EXAMPLE 7

This Example shows the release of H376/95 from the anionic polymer iota-Carrageenan in the absence of a neutral gelling polymer and analysed in different artificial media.

| | |
|---|---|
| H376/95 | 50.5 mg |
| Iota-Carrageenan | 200.0 mg |
| Sodium stearyl fumarate | 2.5 mg |
| Tablet weight | 253 mg |

Tablets were manufactured through direct compression, according to Example 1. Analyses were performed separately in different dissolution baths, similar to Example 6. FIG. 7 shows how the release rate in pH 1 is slower compared to the release in pH 6.8. This effect is not shown when using any other homopolymer we have tested as matrix polymer.

EXAMPLE 8

This Example shows the release of Compound A from a blend with the composition ratio (50:50) of PEO 4M and iota-Carrageenan. Tablets were analysed for 24 hours in different media.

| | Weight (mg) |
|---|---|
| Compound A | 50.0 |
| Iota-Carrageenan (Fluka) | 100.0 |
| PEO, 4 M (Union Carbide) | 100.0 |
| PRUV ™ | 2.5 |

The active ingredient was mixed manually with the polymers and lubricant. The mixture was directly compressed into tablets.

EXAMPLE 9

This Example shows the release of Compound A from a blend with the composition ratio (50:50) of HPMC, 10 000 cps and iota-Carrageenan. Tablets were analysed for 24 hours in different media.

| | Weight (mg) |
|---|---|
| Compound A | 50.0 |
| Iota-Carrageenan (Fluka) | 100.0 |
| HPMC, 10 000 cps | 100.0 |
| PRUV ™ | 2.5 |

The active ingredient was mixed manually with the polymers and lubricant. The mixture was directly compressed into tablets.

Assessment of Cumulative Release of Compound A from Tablets of Examples 8 and 9

Two individual tablets were tested for drug release in 900 ml media using a USP dissolution apparatus 2 (paddle+basket[1]) at 50 rpm and 37° C. The dissolution media used were 0.1M hydrochloric acid (pH 1) and 0.1M sodium phosphate buffer (pH 6.8) with 5% ethanol added to improve drug solubility. The addition of ethanol was verified to not significantly affect the rate of release of these compositions. In-line quantitation was performed using the C Technologies fibre optic system with 235 nm as the analytical wavelength when 0.1 M HCl was used as the dissolution media and with 250 nm as the analytical wavelength when modified phosphate buffer pH 6.8 was used as the dissolution media. 350 nm was used as the reference wavelength with both media.

[1 A custom made quadrangular basket of mesh wire, soldered in one of its upper, narrow sides to the end of a steel rod. The rod is brought through the cover of the dissolution vessel and fixed by means of two Teflon nuts, 3.2 cm from the centre of the vessel. The lower edge of the bottom of the basket is adjusted to be 1 cm above the paddle. The basket is directed along the flow stream with the tablet under test standing on its edge.]

EXAMPLE 10

This Example shows the release of Compound B from a blend with a composition ratio (50:50) of PEO 4M and iota-Carrageenan.

| | Weight (mg) | Amount (%) |
|---|---|---|
| Compound B | 41.0 | 16 |
| Iota-Carrageenan (Fluka) | 104.0 | 41 ("50") |
| PEO, 4 M (union Carbide) | 104.0 | 41 ("50") |
| PRUV | 2.5 | 1 |

The tablets were made according to Example 9. Release data shown in FIG. 10.

EXAMPLE 11

This Example shows the release of Compound B from a blend with a composition ratio (80:20) of PEO 4M and iota-Carrageenan.

|              | Weight (mg) | Amount (%) |
| --- | --- | --- |
| Compound B | 41.0 | 16 |
| Iota-Carrageenan (Fluka) | 41.8 | 17 ("20") |
| PEO, 4 M (union Carbide) | 167.2 | 66 ("80") |
| PRUV | 2.5 | 1 |

The tablets were made according to Example 9. Release data shown in FIG. 10.

EXAMPLE 12

This Example shows the release of Compound B from a blend with a composition ratio (50:50) of HPMC, 10 000 cps and iota-Carrageenan.

|              | Weight (mg) | Amount (%) |
| --- | --- | --- |
| Compound B | 41.0 | 16 |
| Iota-Carrageenan (Fluka) | 104.0 | 41 ("50") |
| HPMC, 10 000 cps (60SH) | 104.0 | 41 ("50") |
| PRUV | 2.5 | 1 |

The tablets were made according to Example 9. Release data shown in FIG. 11.

EXAMPLE 13

Direct Compression of Compound C with HPMC 10 000 cPs.

The active substance and excipients material has been mixed in a beeting vat The blend was lubricated with sodiumstearylfumarate and compressed into tablets using an exenterpress.

|              | Weight | Amount |
| --- | --- | --- |
| Compound C | 50 mg | 16.2% |
| HPMC 10 000 cPs | 255.0 mg | 82.8% |
| Sodium stearyl fumarate | 2.5 mg | 1.0% |

Release Rate Data

| Time (min) | % released in buffer pH 1.1 | % released in buffer pH 6.8 |
| --- | --- | --- |
| 0 | 0 | 0 |
| 15 | — | — |
| 30 | 8 | — |
| 45 | — | — |
| 60 | 13 | 7 |
| 120 | 20 | 12 |
| 180 | 26 | — |
| 240 | 31 | 19 |
| 360 | 40 | 25 |
| 480 | 48 | 31 |
| 600 | 55 | 36 |
| 720 | 61 | 41 |
| 840 | 66 | 45 |
| 960 | 71 | 49 |
| 1080 | 75 | 53 |
| 1200 | 79 | 56 |

Direct Compression of Compound C with HPMC 10 000 cPs and iota-Carrageenan, Ratio 50:50

The active substance and excipients material has been mixed in a beeting vat. The blend was lubricated with sodiumstearylfumarate and compressed into tablets using an exenterpress.

|              | Weight | Amount |
| --- | --- | --- |
| Compound C | 50 mg | 16.2% |
| HPMC 10 000 cPs | 127.0 mg | 41.4% |
| Iota-Carrageenan (Fluka) | 127.0 mg | 41.4% |
| Sodium stearyl fumarate | 3.0 mg | 1.0% |

Release Rate Data

| Time (min) | % released in buffer pH 1.1 | % released in buffer pH 6.8 |
| --- | --- | --- |
| 0 | 0 | — |
| 15 | — | — |
| 30 | 3 | — |
| 45 | — | — |
| 60 | 4 | 4 |
| 120 | 7 | 8 |
| 180 | 10 | — |
| 240 | 12 | 16 |
| 360 | 17 | 27 |
| 480 | 22 | 38 |
| 600 | 27 | 51 |
| 720 | 32 | 63 |
| 840 | 37 | 75 |
| 960 | 41 | 87 |
| 1080 | 46 | 94 |
| 1200 | 50 | 97 |

Release rates were determined as follows. Three individual tablets were tested for drug release in 900 ml media using a USP dissolution apparatus 2 (paddle+basket[1]) at 50 rpm and 37° C. The dissolution media used were 0.1 M hydrochloric acid (pH 1) and 0.1 M sodium phosphate buffer (pH 6.8). In-line quantitation was performed using the C Technologies fibre optic system with 220 nm as the analytical wavelength when 0.1 M HCl was used as the dissolution media and with 260 nm as the analytical wavelength when phosphate buffer pH 6.8 was used as the dissolution media 350 nm was used as the reference wavelength with both media. For the first two hours of the analysis the release value was measured every 15 minutes, and then every hour for the remainder of the analysis.

[1] A custom made quadrangular basket of mesh wire, soldered in one of its upper, narrow sides to the end of a steel rod. The rod is brought through the cover of the dissolution vessel and fixed by means of two Teflon nuts, 3.2 cm from the centre of the vessel. The lower edge of the bottom of the basket is adjusted to be 1 cm above the paddle. The basket is directed along the flow stream with the tablet under test standing on its edge.

EXAMPLE 14

|              | Weight | Amount |
| --- | --- | --- |
| Compound D | 100 mg | 20% |
| HPMC 10 000 cPs | 200 mg | 40% |
| Iota-Carrageenan | 200 mg | 40% |
| Sodium stearyl fumarate | 5 mg | 1% |

This formulation can be prepared as described in Example 13.

The invention claimed is:

1. An oral pharmaceutical formulation comprising
   iota-carrageenan;
   one or more neutral gelling polymers; and
   a basic pharmaceutically active ingredient,
   wherein the formulation inhibits release of the basic pharmaceutically active ingredient from the formulation at acidic pH, and
   wherein the basic pharmaceutically active ingredient is Ph(3-Cl)(5-OCHF$_2$)—(R)CH(OH)C(O)—(S)Aze-Pab(OMe).

2. The formulation as claimed in claim 1 wherein the neutral gelling polymer is a polyethylene oxide, polyethylene glycol or a mixture of two or more different polyethylene oxides.

3. The formulation as claimed in claim 1 wherein the neutral gelling polymer is an hydroxypropylmethyl cellulose, or a mixture of two or more different hydroxypropylmethyl celluloses.

4. The formulation as claimed in claim 1 wherein the neutral gelling polymer is a mixture of an hydroxypropylmethyl cellulose and a polyethylene oxide.

5. The formulation as claimed in claim 1 wherein the ratio of neutral gelling polymer to iota-carrageenan is in the range 20:80 to 80:20.

6. A process for preparing the formulation as claimed in claim 1, the process comprising mixing the iota-carrageenan, the one or more neutral gelling polymers and the basic pharmaceutically active ingredient.

7. A method of treating a cardiovascular disorder in a patient suffering from, or at risk of, said disorder, which comprises administering to the patient a therapeutically effective amount of a pharmaceutical formulation as claimed in claim 1.

\* \* \* \* \*